(12) United States Patent
Saaski

(10) Patent No.: US 7,608,463 B2
(45) Date of Patent: Oct. 27, 2009

(54) ENHANCED WAVEGUIDE AND METHOD

(75) Inventor: Elric W. Saaski, Bothell, WA (US)

(73) Assignee: Research International, Inc., Monroe, WA (US)

( * ) Notice: Subject to any disclaimer, the term of this patent is extended or adjusted under 35 U.S.C. 154(b) by 97 days.

(21) Appl. No.: 11/825,943

(22) Filed: Jul. 10, 2007

(65) Prior Publication Data

US 2007/0259441 A1 Nov. 8, 2007

Related U.S. Application Data

(62) Division of application No. 10/470,216, filed as application No. PCT/US02/03356 on Feb. 1, 2002, now Pat. No. 7,276,368.

(60) Provisional application No. 60/265,605, filed on Feb. 2, 2001.

(51) Int. Cl.
*G01N 21/76* (2006.01)

(52) U.S. Cl. .............. 436/172; 422/55; 422/57; 422/58; 422/63; 422/82.05; 422/82.06; 422/82.11; 435/287.2; 435/287.3; 435/287.9; 435/288.7; 435/808; 436/43; 436/47; 436/164; 436/518; 436/524; 436/527; 436/805

(58) Field of Classification Search .............. 422/55, 422/57, 58, 63, 82.05, 82.06, 82.11; 435/287.2, 435/287.3, 287.9, 288.7, 808; 436/43, 47, 436/164, 172, 518, 524, 527, 805
See application file for complete search history.

(56) References Cited

U.S. PATENT DOCUMENTS 3,604,927 A 9/1971 Hirschfeld

| 4,050,895 A | 9/1977 | Hardy et al. |
| 4,133,639 A | 1/1979 | Harte |
| 4,257,671 A | 3/1981 | Barbaudy et al. |
| 4,321,057 A | 3/1982 | Buckles |
| 4,399,099 A | 8/1983 | Buckles |
| 4,447,546 A | 5/1984 | Hirschfeld |
| 4,477,578 A | 10/1984 | Miles et al. |

(Continued)

FOREIGN PATENT DOCUMENTS

EP 0 128 723 A2 12/1984

(Continued)

OTHER PUBLICATIONS

Li Li, C. et al., "Application of Electromodulated Fluorescence To The . . . ", Langmuir 2000, vol. 16, No. 10, pp. 4672-4677, American Chemical Society, U.S., 2000.

(Continued)

*Primary Examiner*—Christopher L Chin
(74) *Attorney, Agent, or Firm*—Gregory W. Moravan

(57) ABSTRACT

An optical assay apparatus having an optical filter, an optical sensor with a light ray redirection portion and an assay sensing portion, and a filter to block certain wavelengths of excitation light rays and to pass certain wavelengths of signal recovery light rays from the optical sensor. A method for performing an assay that includes providing at least one assay station, moving the optical sensor into position over a respective fluid in at least one assay station, immersing the assay sensing portion in the respective fluid, and removing the assay sensing portion from the respective fluid.

20 Claims, 16 Drawing Sheets

U.S. PATENT DOCUMENTS

| | | | |
|---|---|---|---|
| 4,558,014 A | 12/1985 | Hirschfeld et al. | |
| 4,582,809 A | 4/1986 | Block et al. | |
| 4,595,833 A | 6/1986 | Sting | |
| 4,654,532 A | 3/1987 | Hirschfeld | |
| 4,671,938 A | 6/1987 | Cook | |
| 4,716,121 A | 12/1987 | Block et al. | |
| 4,844,869 A | 7/1989 | Glass | |
| 4,852,967 A | 8/1989 | Cook et al. | |
| 4,909,990 A | 3/1990 | Block et al. | |
| 5,055,408 A | 10/1991 | Higo et al. | |
| 5,061,857 A | 10/1991 | Thompson et al. | |
| 5,093,569 A | 3/1992 | Krumboltz et al. | |
| 5,111,221 A | 5/1992 | Fare et al. | |
| 5,152,962 A | 10/1992 | Lackie | |
| 5,156,976 A | 10/1992 | Slovacek et al. | |
| 5,225,374 A | 7/1993 | Fare et al. | |
| 5,242,797 A | 9/1993 | Hirschfeld | |
| 5,268,486 A | 12/1993 | Waggoner et al. | |
| 5,290,398 A | 3/1994 | Feldman et al. | |
| 5,340,715 A | 8/1994 | Slovacek et al. | |
| 5,359,681 A | 10/1994 | Jorgenson et al. | |
| 5,399,866 A | 3/1995 | Feldman et al. | |
| 5,430,813 A | 7/1995 | Anderson et al. | |
| 5,442,448 A | 8/1995 | Knoll | |
| 5,468,606 A | 11/1995 | Bogart et al. | |
| 5,492,674 A | 2/1996 | Meserol | |
| 5,494,793 A | 2/1996 | Schindele et al. | |
| 5,512,492 A | 4/1996 | Herron et al. | |
| 5,525,466 A | 6/1996 | Slovacek et al. | |
| 5,545,517 A | 8/1996 | Thompson et al. | |
| 5,569,766 A | 10/1996 | Waggoner et al. | |
| 5,582,796 A | 12/1996 | Carey et al. | |
| 5,606,170 A | 2/1997 | Saaski et al. | |
| 5,719,063 A | 2/1998 | Block | |
| 5,858,800 A | 1/1999 | Shigemori et al. | |
| 5,885,529 A | 3/1999 | Babson et al. | |
| 6,007,996 A | 12/1999 | McNamara et al. | |
| 6,008,057 A | 12/1999 | Glass et al. | |
| 6,082,185 A | 7/2000 | Saaski | |
| 6,103,535 A * | 8/2000 | Pilevar et al. | 436/518 |
| 6,136,611 A | 10/2000 | Saaski et al. | |
| 6,192,168 B1 | 2/2001 | Feldstein et al. | |
| 6,316,274 B1 * | 11/2001 | Herron et al. | 436/518 |

FOREIGN PATENT DOCUMENTS

| | | |
|---|---|---|
| EP | 0 535 690 A1 | 4/1993 |
| JP | S63-273042 | 11/1988 |
| JP | H02-191674 | 7/1990 |
| JP | H03-272466 | 12/1991 |
| JP | H04-225144 | 8/1992 |
| JP | H05-118991 | 5/1993 |
| JP | H05-203574 | 8/1993 |
| JP | H06-308031 | 11/1994 |
| JP | H07-063756 | 3/1995 |
| JP | H07-103901 | 4/1995 |
| JP | H07-174692 | 7/1995 |
| JP | H07-181132 | 7/1995 |
| JP | H07-318481 | 12/1995 |
| JP | H09-257806 | 10/1997 |
| JP | 2000-171391 | 6/2000 |
| JP | 2000-325295 | 11/2000 |
| JP | 2000-356585 | 12/2000 |
| WO | WO 84/00817 | 3/1984 |
| WO | WO 90 09574 | 8/1990 |
| WO | WO 92/08966 | 5/1992 |
| WO | WO9531711 | 11/1995 |

OTHER PUBLICATIONS

Anderson, George P. et al., "A Fiber Optic Biosensor: Combination Tapered Fibers Designed For Improved Signal . . . ", Bio-Sensors & Bioelectronics 8:249-256, 1993.

Anis, N.A., et al., "A Fiber-Optic Immunosensor For Detecting Parathion", Analytical Letters 25(4):627-635, 1992.

Gao, Harry H. et al., "Tapered Fiber Tips For Fiber Optic Biosensors", Optical Engineering 34(12):3465-3470, 1995.

Glass, Thomas R., et al, "Effect Of Numerical Aperture On Signal Level In Cylindrical Waveguide Evanescent Fluorosensors", Applied Optics 26(11):2181-2187, 1987.

Golden, Joel P. et al., "Fluorometer And Tapered Fiber optic Probes For Sensing In The Evanscent Wave", Optical Engineering 31(7):1458-1462, 1992.

Golden, Joel P. et al., "Portable Multichannel Fiber Optic Biosensor For Field Detection", 1997 Optical Engineering 36(4), 1008-1013, Apr. 1997.

Golden, Joel P. et al., "Ray Tracing Determination Of Evanescent Wave Penetration Depth . . . ", Chemical, Biochemical, and Environmental Fiber Sensors IV 1796:9-13, 1992.

Hale, Z.M., et al., "Fluorescent Sensors Based On Tapered Single-Mode Optical Fibers", Sensors And Actuators B. 17:233-240, 1994.

Hobbs, J.R., "Fluorescence Reveals Toxins On Antibody-Coated Fiberoptic Probe", Laser Focus World 28(5):83-86, 1992.

Huber, W., et al., "Direct Optical lmmunosensing (Sensitivity and Selectivity)", Sensors And Actuators B. 6:122-126, 1992.

Jorgenson, R.C., et al., "A Fiber-Optic Chemical Sensor Based On Surface Plasmon Resonance", Sensors And Actuators B. 12, (3):213-220, 1993.

Jung, C.C., et al., "Chemical Electrode Surface Plasmon Resonance Sensor", Sensors And Actuators B. 32(2):143-147, 1996.

Ligler, F.S., et al., "Evanescent Wave Fiber Optic Biosensor", Proc. Biosensors, A.P.F. Turner, ed., pp. 308-315, 1992.

Rogers, Kim R., et al., "Acetylcholine Receptor Fiber-Optic Evanescent Fluorosensor", Analytical Biochemistry 182:353-359, 1989.

Wong, R.B., et al., "Reusable Fiber-Optic-Based lmmunosensor For Rapid Detection Of Imazethapyr Herbicide", Analytica Chimica Acta, 279:141-147, 1993.

* cited by examiner

ENHANCED WAVEGUIDE AND METHOD

This application is a divisional of U.S. application Ser. No. 10/470,216 filed on Jul. 25, 2003 now U.S. Pat. No. 7,276,368, which is the National Stage of International Application No. PCT/US02/03356 filed on Feb. 1, 2002, which claims the benefit, under 35 U.S.C. §119(e) of U.S. Application No. 60/265,605 filed on Feb. 2, 2001. Under 37 C.F.R. §1.57, each of the identified Applications is hereby incorporated by reference in this divisional Application.

FIELD OF THE INVENTION

This invention relates generally to optical methods and apparatus for chemical and biochemical assays, and more particularly to fiber optics-based methods and apparatus for such assays.

BACKGROUND OF THE INVENTION

There exists a need for a highly sensitive and specific technology directed to the detection of human pathogens and toxins in food, water, and the environment. It is very difficult to effectively detect organisms in natural fluids such as milk, blood, sewage and meat products at low concentration and to discriminate between pathogenic and harmless species. Conventional bioassay methods are commonly designed for samples on the order of a few cubic centimeters, and the extraction or concentration of pathogenic material from larger volumes to met sensitivity requirements creates additional challenges.

One of the most promising strategies for performing pathogen assays on raw, unpurified samples is based on sensors that harness biological ligand-receptor interactions to identify specific compounds. Examples of approaches that implement such a strategy include fiber optic evanescent wave sensors and surface plasmon resonance sensors.

An electromagnetic wave, traveling through one material, which is reflected at a dielectric interface produces an exponentially decaying electric field within the second material on the opposite side of the interface. At optical frequencies this is termed the evanescent wave effect, and at radio frequencies this phenomenon is often called a "skin effect." The penetration depth within the second material, the evanescent wave region, is a small fraction of a wavelength, yet greater in size than most optical labels 100 such as light- or fluorescence-producing reporter molecules, light-absorbing or scattering molecules, and colloidal particles and microspheres. These labels can be used to monitor or produce optical changes in the evanescent region, or modify the propagation of light in the adjacent dielectric, providing a fundamental means of detecting target materials that are close to the surface while discriminating against those far away. In particular, by coating the interface with a capture agent that is specific for a microscopic or molecular target of interest, exquisitely sensitive optical-based sensors can be created.

In one competitive assay technique, fluorophore-labeled antigen 104, together with the sample to be tested, is exposed to the coating of capture antibody on the fiber, and the labeled antigen competes for antibody binding sites with non-tagged analyte 106 in the test sample. The evanescent field produced by light 108 passing through the fiber 102 then excites the fluorophores into light emission 110, and the fiber itself conveniently acts as a return waveguide for the fluorescent signal. In this example, the strength of the fluorescent signal is inversely related to the analyte concentration in the test sample. Alternatively, a non-competitive technique, such as a sandwich-format assay, can be used, in which case the fluorescent signal is directly related to the analyte concentration in the test sample. High sensitivity and specificity can be achieved for a wide range of metals, toxins, proteins, viruses, living and dead bacteria, and spores, through the use of bound target-specific agents 100 such as chelating agents, antibodies, crown ethers and the like, combined with appropriate optical labels that luminesce, fluoresce or alter light transport by the waveguide. In applications where pathogens will be infrequently found, cost per assay may be low since the sensor remains active until the capture agents have been substantially neutralized by the binding of the target material.

For surface plasmon resonance sensing, FIG. 1B shows a thin layer of metal 110, such as gold, applied to a core portion 112 of an optical fiber 114 from which the cladding 116 of the fiber has been partly removed. The evanescent electric field produced by light 118 passing through the fiber 114 excites surface plasmon waves 120 on the outer surface of the metal 110. When white light is passed through the fiber 114, the excitation of a surface plasmon wave causes a dip in the spectrum of the light passing through the fiber, with the dip occurring at a resonance wavelength which is a function of the complex indices of refraction of the fiber core, the metal layer, and the solution surrounding the fiber, as well as the incidence angle of the light. Light passing through the fiber 114 can be returned by a mirror 122, or can be passed through the distal end of the fiber (in the absence of a mirror) for optical processing and analysis, as is well known to those skilled in the art. Any change in the index of refraction of the solution is detectable, and molecules binding to the surface of the metal 110 can then be detected if they have an index of refraction that is different from the bulk solution. Coating the metal layer 110 with target-specific capture molecules (not shown), which react with target analytes within a sample solution, then allows detection of reactions (such as antigen-antibody reactions and reduction-oxidation reactions) on the surface of the metal.

Fiber optic evanescent wave sensors are the subject of a number of U.S. patents, including the following, the disclosures of each being incorporated herein by reference: U.S. Pat. No. 4,447,546, to Hirschfeld et al., entitled "Fluorescent Immunoassay Employing Optical Fiber in Capillary Tube"; U.S. Pat. No. 4,558,014, to Hirschfeld et al., entitled "Assay Apparatus and Method"; U.S. Pat. No. 4,582,809, to Block et al., entitled "Apparatus Including Optical Fiber for Fluorescence Immunoassay"; U.S. Pat. No. 4,654,532, to Hirschfeld, entitled "Apparatus for Improving the Numerical Aperture at the Input of a Fiber Optic Devices"; U.S. Pat. No. 4,716,121, to Block et al., entitled "Fluorescent Assays, Including Immunoassays, with Feature of Flowing Sample"; U.S. Pat. No. 4,909,990, to Block et al., entitled "Immunoassay Apparatus"; U.S. Pat. No. 5,242,797, to Hirschfeld, entitled "Nucleic Acid Assay Method"; U.S. Pat. No. 5,061,857, to Thompson et al., entitled "Waveguide-Binding Sensor for Use With Assays"; U.S. Pat. No. 5,430,813, Anderson et al., entitled "Mode-Matched, Combination Taper Fiber Optic Probe"; U.S. Pat. No. 5,152,962, to Lackie, entitled "Immunoassay Apparatus"; U.S. Pat. No. 5,290,398, to Feldman et al., entitled "Synthesis of Tapers for Fiber Optic Sensors"; and U.S. Pat. No. 5,399,866, to Feldman et al., entitled "Optical System for Detection of Signal in Fluorescent Immunoassay." Fiber optic surface plasmon resonance sensors are the subject of U.S. Pat. No. 5,359,681 to Jorgenson et al., entitled "Fiber Optic Sensor and Methods and Apparatus Relating Thereto," the disclosure of which is incorporated herein by reference.

For evanescent wave sensors, it is desirable to optimize the magnitude of the evanescent electric field as well as to optimize the optical properties of the return path for the detected fluorescence. The above-identified patents describe numerous optimization approaches, including attempts to match the numerical aperture of various system components and to improve system numerical aperture. Numerical aperture is a measure of the largest angle, relative to the optical axis of a system, which a ray of light can have and still pass through the system. Each component in an optical system will have its own unique limiting numerical aperture, and the maximum system numerical aperture will be determined by the system component having the lowest numerical aperture. The system numerical aperture is a key parameter in optical sensing since transferred power is typically proportional to its square. Good design practice and cost efficiencies require system components to have matching numerical apertures.

One well-known approach of matching numerical apertures employs tapered or cone-shaped waveguides. In addition to providing numerical aperture matching, tapering the active, analyte-sensitive portion of the optical fiber maintains a substantial fraction of the input light near the critical angle, thereby maintaining a high magnitude evanescent field. However, there is also a constant loss of light along the sensor fiber as the taper acts upon rays that are already only weakly guided and causes them to exceed the critical angle.

In order for white light to propagate in an optical fiber used in connection with a surface plasmon resonance sensor, the fiber must have a large enough diameter to support the longest wavelength of light. Also, a large diameter fiber propagates higher numerical aperture light, which makes it easier to excite surface plasmon waves in metal films of a thickness readily fabricated by conventional processes. As a consequence, multi-mode fibers are used which propagate light over a range of angles. However, this range of angles results in a less distinct resonance effect, because each angle of propagation results in a different resonance wavelength.

FIG. 2A shows the theoretical resonance curves for various propagation angles relative to the optical axis of the fiber core, assuming a 55 nm thick layer of gold on a silica optical fiber core immersed in water. The overall resonance detected is a superposition of the resonance effects for each of the various angles of propagation. FIG. 2B shows the integration of individual theoretical resonance curves for propagation angles from 0 to 23.6 degrees, assuming a sine-squared distribution of optical power at the various propagation angles. The significant signal degradation associated with current approaches to surface plasmon resonance sensing is seen by comparing the resonance curve of FIG. 2B with the individual resonance curve of, for example, 23.6 degrees in FIG. 2A.

The first evanescent waveguide sensors, described in the early 1980's, were for substantially cylindrical waveguides, that is, waveguides with circular cross-sections in which light uniformly filled the entire cross-sectional area. Recent development has strongly emphasized planar waveguides excited by collimated light beams. In these devices, light is only contained in one dimension and lateral spreading is totally defined by excitation optics. This substantial shift has occurred primarily due to an interest in creating multianalyte assay arrays by printing a linear or two-dimensional pattern of capture agent spots on one surface of the planar waveguide within the illumination path of the light beam, and then monitoring for an optical signal from individual analyte-specific spots with a CCD detector array or photomultiplier on the other side of the slab waveguide.

However, the planar approach has some other weaknesses in addition to its limited light guiding ability. Due to the typically small size of individual assay spots it is a challenge to effectively contact each dot with the entire fluid sample. This is of particular significance when foodstuffs are tested for pathogens. Regulations may require, because of high health risks at extremely low pathogen levels, that assay samples of 300 cubic centimeters or more be utilized. By way of example, the acceptance limit set by the US Department of Agriculture for *Escherichia coli* O157:H7 is one organism per 25 gm of sample. It is very difficult to effectively detect organisms at such a low concentration with methods based on bioassay dots of typically 1 mm^2 or less area. In addition, sample heterogeneity becomes an issue when raw food samples are examined. Fat globules and other non-toxic components may adhere non-specifically to the sensor or physically block contact with the target, reducing the effective sensitivity. Samples may also be viscous which increases the mass transfer boundary layer thickness and decreases the diffusive mass transport rates. These factors may yield low signal levels and create poor assay statistics where the target is a low, yet lethal concentration of a human or animal pathogen.

Analyte mass-diffusion boundary layers are also typically thicker for planar structures than for solids of revolution, such as cylinders. For related reasons a planar geometry may be more difficult to clean if the assay involves a multi-step protocol such as a sandwich immunoassay, or if it is desired to reuse the sensor. Finally, for applications such as food safety the number of target pathogens may be only one to six, calling into question the value of low sensitivity array techniques that require sophisticated and possibly costly CCD or photomultiplier signal recovery techniques.

Although evanescent wave and surface plasmon resonance sensors show great promise for use in medical and food safety applications, those skilled in the art understand that the current technology is less than optimal in a number of respects, including those disadvantages identified above.

SUMMARY OF THE INVENTION

In accordance with the present invention, an optical assay apparatus includes a light source module and an optical sensor. The light source module produces light having a range of propagation angles. The sensor includes a light adjusting portion and an assay sensing portion. The light adjusting portion receives the light produced by the light source module and provides light having a propagation angle that is substantially constant to the assay sensing portion.

In one embodiment, the light source module produces light having propagation angles ranging from a lower, non-zero limit. This may be accomplished by including an obscuration which blocks light having propagation angles below this limit. In one embodiment, the light adjusting portion of the sensor may include a reflector which receives, as incident light, the light produced by the light source module and produces, as reflected light, the light having a substantially constant propagation angle. The assay sensing portion of the sensor may be a waveguide coated with sensor molecules suitable for performing evanescent wave sensing operations, or may be a waveguide coated with a thin metallic film suitable for performing surface plasmon resonance sensing operations.

In one embodiment, the sensor may be coupled with the light source module by an interrogation module that includes a window in which a waveguide is integrated. The waveguide transmits the light produced by the light source module to the sensor. The waveguide may be an optical fiber with an angled end having a reflective surface to create a right-angle reflector. The waveguide may be embedded in the window in a slot containing an opaque material to prevent back-scattering of excitation light from the waveguide into optical components included within the interrogation module.

In one embodiment, the sensor and interrogation module are mounted in an automated assay platform that provides two-dimensional or three-dimensional movement of the sensor so that it can be sequentially immersed in solutions required to perform a particular assay protocol. While the sensor is immersed in a particular liquid, the system provides oscillatory movement of the sensor and/or rotary movement of the contacted liquid to increase evanescent wave region reaction rates with targeted analytes and/or reagents.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

An optical assay apparatus and method is described, with certain specific details set forth in order to provide a thorough understanding of various embodiments of the present invention. However, one skilled in the art will understand that the present invention may be practiced without these details. In other instances, well-known structures and operations are not shown or discussed in detail in order to avoid obscuring the description of the embodiments of the invention.

Figure 3:
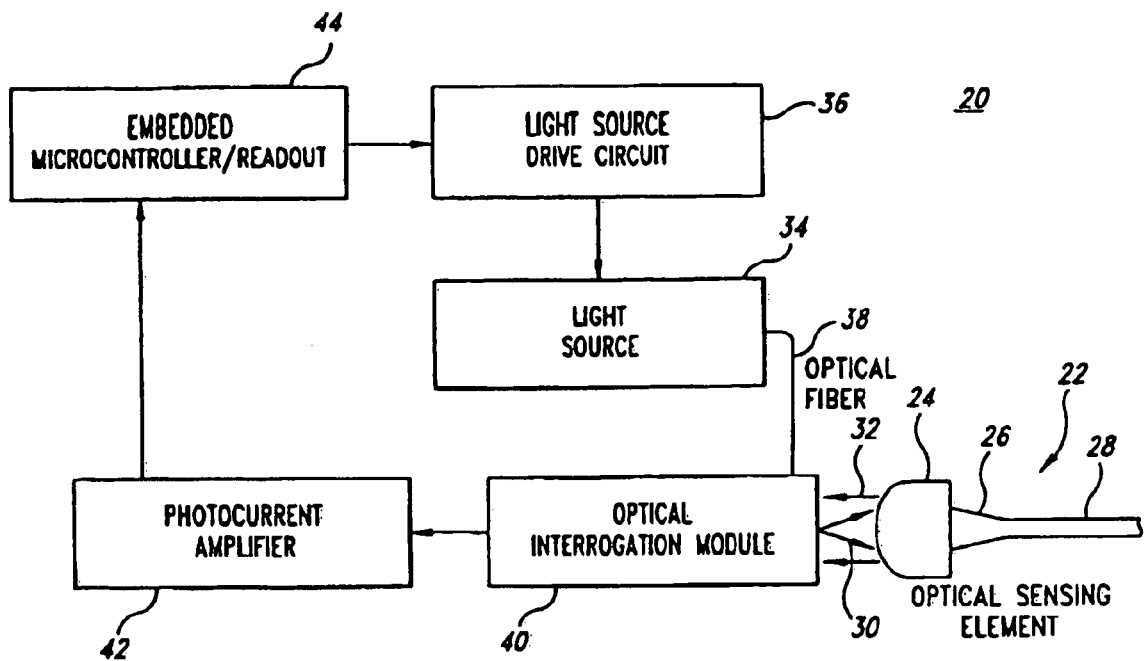
FIG. 3 is a functional block diagram that depicts an assay system in accordance with an embodiment of the present invention.

FIG. 3 is a functional block diagram that depicts an assay system 20. An optical sensing element 22 includes a lens portion 24, a reflector portion 26, and a sensing waveguide or fiber portion 28, as will be described in further detail below. The sensing element 22 receives excitation light 30 and returns signal recovery light 32. The excitation light 30 is produced by a light source module 34, under control of a drive circuit 36. The light source module 34 provides the excitation light via a waveguide or optical fiber, such as source fiber 38. An interrogation module 40 receives the signal recovery light 32, and can also advantageously optically couple the sensing element 22 with the excitation light 30 transmitted via the source fiber 38. The optical interrogation module 40 includes optical devices, such as lenses, and transducers, such as photodetectors, to produce an electrical signal functionally related to the signal recovery light 32. The electrical signal is amplified by photo-current amplifier 42 which provides the amplified signal to a microcontroller 44. The microcontroller 44 then interprets the amplified signal, and provides the sensing operation results in the form of a readout or printout, or stores the results for later analysis. The microcontroller 44 also can control operation of the light source drive circuit 36.

Those skilled in the art will appreciate that the assay system depicted in FIG. 3 is a simplified block diagram showing components whose configuration and function is well-known. Details concerning portions of the light source module 34, the optical interrogation module 40, and the sensing element 22 will be described below in connection with the various embodiments of the present invention. Further details regarding the other functional blocks shown in FIG. 3 need not be described herein for those skilled in the art to practice the present invention.

Figure 4:
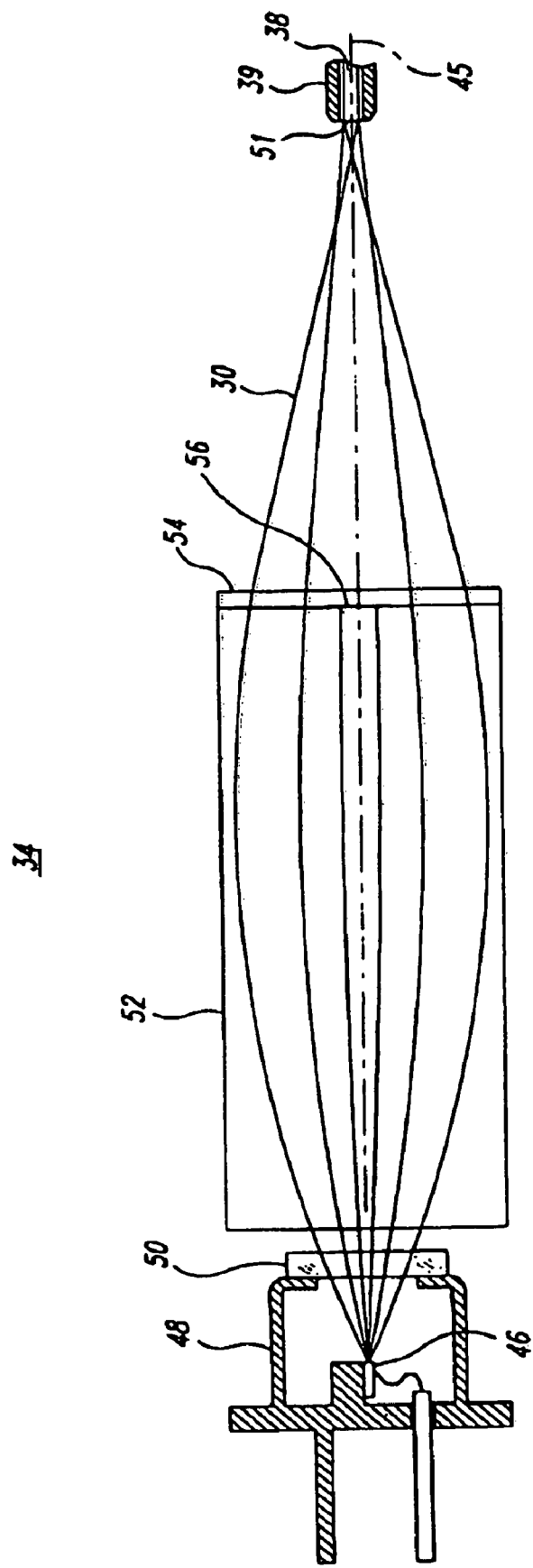
FIG. 4 depicts a portion of a light source module included in the assay system of FIG. 3.

FIG. 4 depicts a portion of the light source module 34 of FIG. 3. The figure depicts a cross-section taken along an optical axis 45. A light source, such as a laser diode 46, is included within a source housing 48 having a window 50. The laser diode 46 produces the excitation light 30, which is focused onto an end 51 of the source fiber 38 by a numerical aperture-adjusting lens 52. The source fiber 38 is held by an optical fiber ferrule 39 used for positioning the end 51 of the fiber at the focal point of the numerical aperture-adjusting lens 52. The source fiber 38 then transfers the excitation light to the sensing element 22, for example, as shown in FIG. 3.

In one embodiment, the laser diode 46 is a commercially available visible laser diode in a standard 9 mm package, operating in the 600 nm to 700 nm waveband and producing an average power of about 1 mW or more. The numerical aperture-adjusting lens 52 is a 3 mm diameter, 0.25 pitch graded refractive index (GRIN) lens. The source fiber 38 is a 200 micron core-diameter optical fiber, which is preferably made of a transmission material such as glass or quartz, since such material generates minimal self-fluorescence and has low scattering losses. However, plastic fibers or other waveguides may be suitable, especially if the distance from the light source module 34 to the sensing element 22 (see FIG. 3) is less than a few meters. In this embodiment, the GRIN lens transforms the approximately 0.4 to 0.6 numerical aperture of the laser diode 46 to approximately 0.22, in keeping with the comparatively low maximum numerical aperture of quartz fibers. A thin (approximately 0.15 mm) transparent glass disk 54 is bonded to the GRIN lens 52 by a transparent adhesive, and includes a circular obscuration 56 of approximately 0.75 mm diameter positioned symmetrically about the optical axis 45. The effect of the obscuration 56 is to eliminate low propagation angle rays from being input to the source fiber 38. If the source fiber 38 is not bent so severely as to promote internal mode conversion, and does not contain large numbers of scattering centers, then light exiting the fiber will have the same angular characteristics as light entering the fiber.

Figure 5:
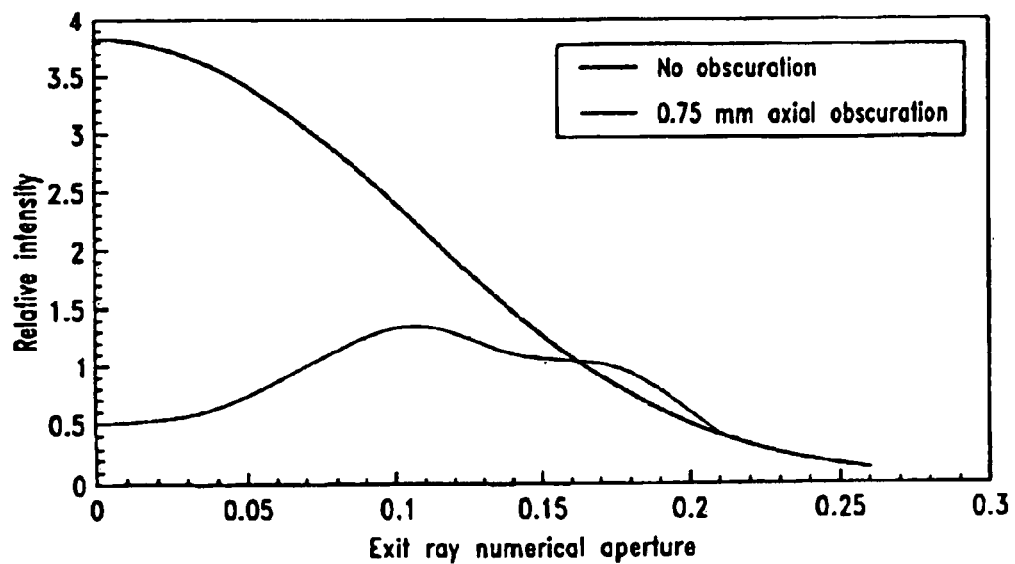
FIG. 5 is a graph that depicts the improved light distribution provided by the light source module of FIG. 4.

FIG. 5 is a graph that shows measurements of the angular distribution of the light exiting from the source fiber 38, with and without the obscuration 56. These measurements correspond to the light source module 34 and source fiber 38 of the particular construction described above. Clearly, the obscuration 56 provides an angular distribution of light with the lower propagation angle rays largely removed, the advantage of which will become apparent in the discussion below. For purposes of convenient presentation, propagation angles relative to the optical axis 45 (see FIG. 4) are represented as numerical aperture values in the graph of FIG. 5.

Figure 6A:
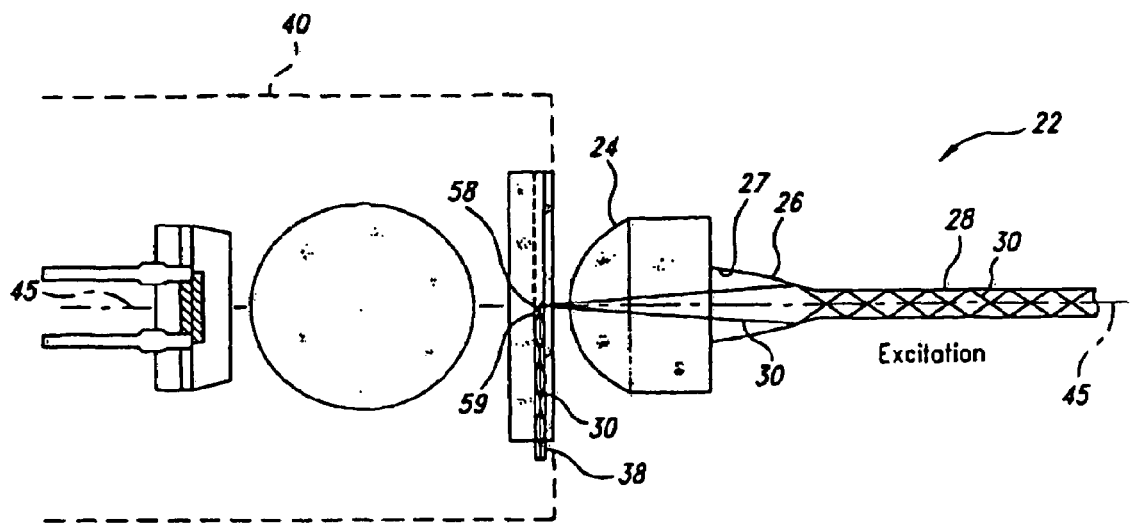
FIG. 6A depicts a portion of an optical interrogation module and of an optical sensing element included in the system of FIG. 3, and shows an excitation light path.

FIG. 6A shows the excitation light 30 passing through the source fiber 38 to a right-angle reflector 58 constructed on a distal end 59 of the fiber. The excitation light 30 then passes into the lens portion 24 of the sensing element 22, reflects off a reflective surface 27 of the reflector portion 26, and passes into the sensing fiber portion 28. The sensing fiber portion 28 may be a core portion of an optical fiber from which the cladding has been removed. Alternatively, the sensing fiber 28 may be a plastic fiber, or any of a variety of suitably adapted waveguide configurations.

Figure 6B:
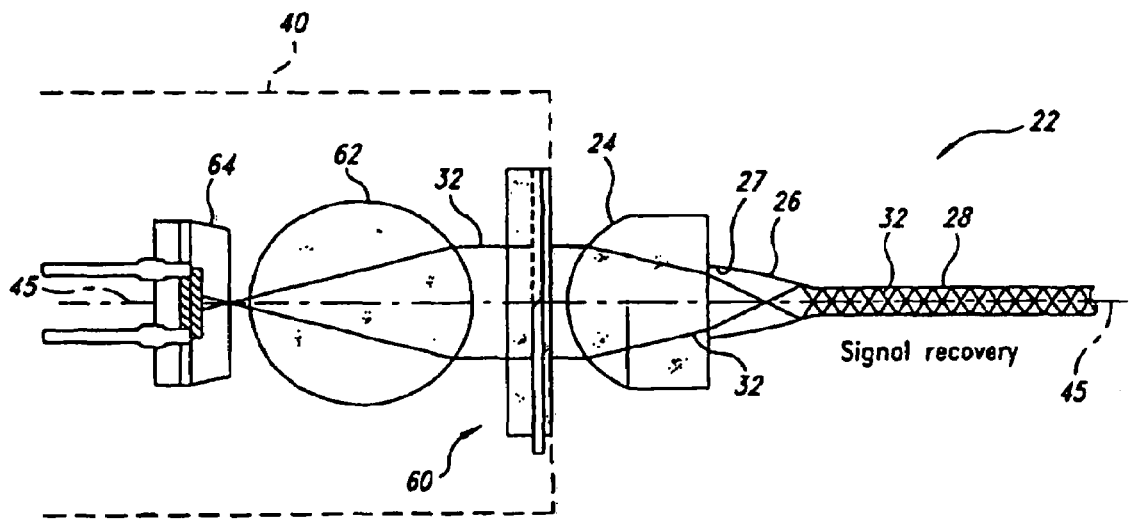
FIG. 6B depicts the portions of the interrogation module and of the optical sensing element of FIG. 6A, and shows a signal recovery light path.

FIG. 6B depicts the return of signal recovery light 32, such as from evanescent field-induced fluorescence, through the sensing fiber 28, reflecting off the reflector 26, refracting through the lens 24, and passing into the interrogation module 40 (also see FIG. 3) through an interrogation window 60. Once inside the interrogation module 40, the signal recovery light 32 is focused by a lens, such as a sapphire ball lens 62, onto a transducer, such as a photodetector 64.

Figure 7A:
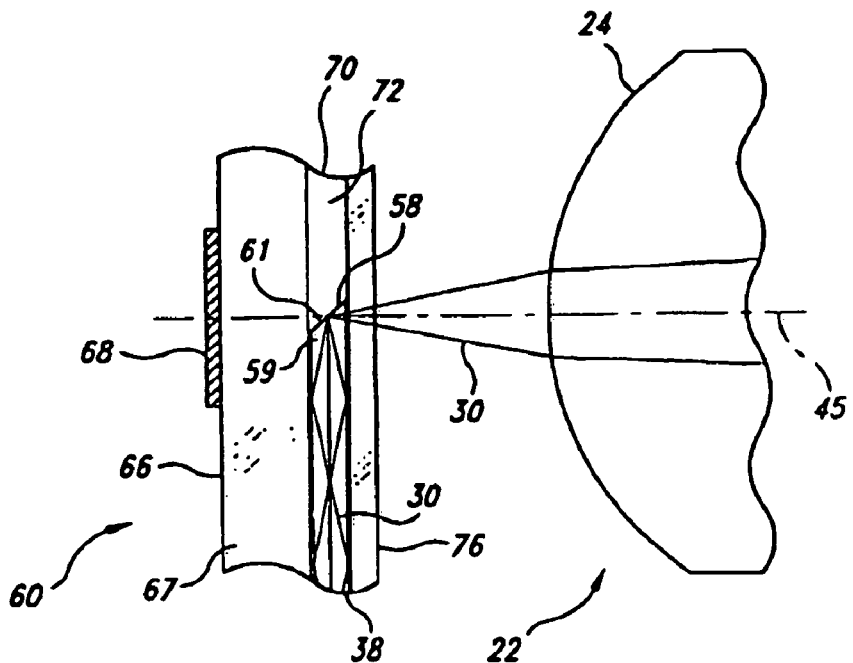
FIG. 7A is a side view that depicts an embodiment of an interrogation module window included in the optical interrogation module of FIG. 6A.

FIG. 7A shows greater details of one embodiment of the interrogation module window 60. The distal end 59 of the source fiber 38 is polished to a 45.degree. mirror finish, and coated with a reflective film 61, to form the right-angle reflector 58. This portion of the source fiber 38 is integrated within the interrogation module window 60, as described in detail herein. The right-angle reflector 58 is oriented so that light within the source fiber 38 emerges from the window 60 generally perpendicular to the window surface, with a numerical aperture of, for example, 0.22.

The interrogation module window 60 includes a laser-line rejection filter film 66 deposited onto one face of a glass plate 67. The primary function of the filter film 66 is to exclude any flare light associated with the excitation light 30 from reaching the optical components included within the interrogation module 40, while providing an unimpeded path for the longer wavelength fluorescent signal recovery light 32 (see FIGS. 6A and 6B). The selection of an excitation source and blocking filter are intimately related to signal recovery and are discussed in that context at a later point. A circular obscuration feature 68 of, for example, approximately 1.5 mm diameter is painted or coated onto the exterior surface of the filter film 66. The obscuration 68 augments the filter film 66 by blocking any back-reflected excitation light 30 which might be reflected off the lens portion 24 of the sensing element 22.

Figure 7B:
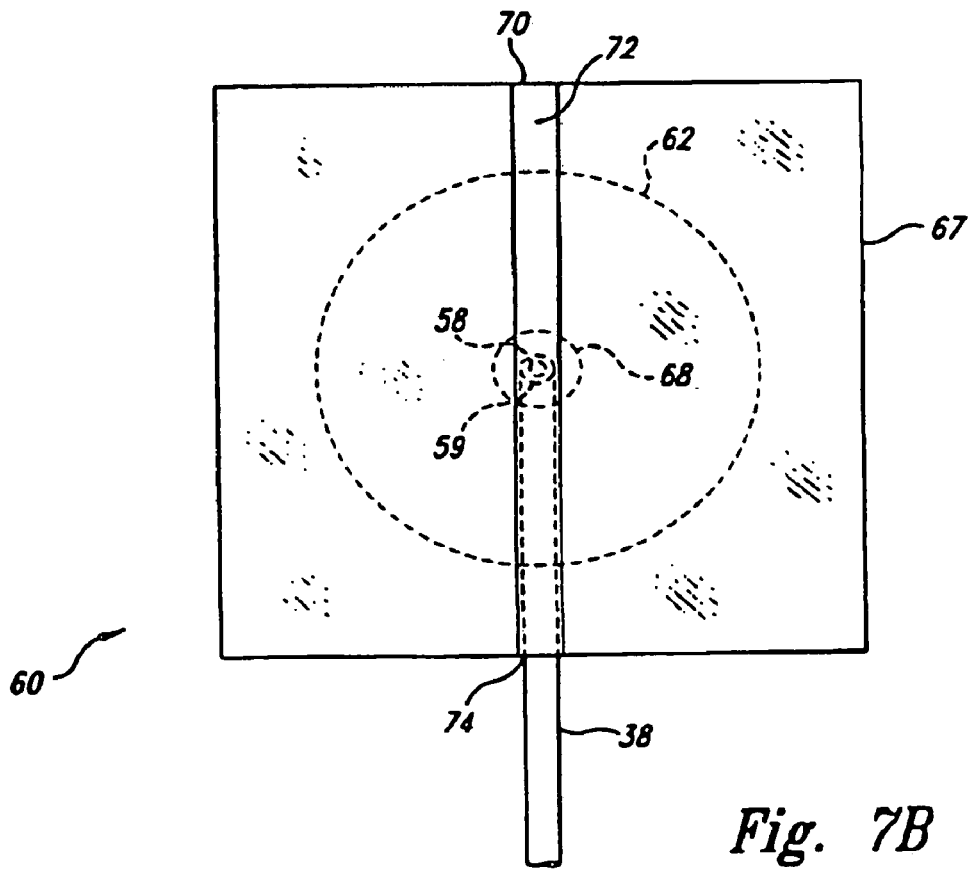
FIG. 7B is a front view of the interrogation module window of FIG. 7A.

Referring to both FIGS. 7A and 7B, a groove 70 is cut into the glass plate 67 on the side opposite the filter film 66. This groove may be cut with a high-speed, water-cooled diamond saw. The slot 70 is then filled with a highly opaque material 72, such as 320 epoxy from Epoxy Technologies of Billerica, Mass. A second, narrower slot 74, equal to the width of the source fiber 38, is then made in the opaque material 72, taking care to position the slot 74 so that it does not break through the opaque material 72 at any point along the length of the slot 74. The source fiber 38 is then positioned in the slot 74 so that it is emitting light at the correct position and in the correct direction, and a thin glass cover plate 76 is pressed against the groove window face to preserve the fiber's position. A transparent material, such as UV adhesive P92 from Summers Optical of Fort Washington, Pa., is then wicked into the void area surrounding the entrapped source fiber 38 to remove any air, and the adhesive is cured.

Both the adhesive and cover plate 76 should be selected to have refractive indices that are approximately the same as the cladding of the source fiber 38 to minimize aberration in the projected beam. Since the excitation light 30 must, upon reflection from the right-angle reflector 58, pass through the cylindrical wall of the source fiber 38, the fiber's wall would otherwise act as a cylindrical lens and distort the shape of the emitted excitation light beam. The opaque material 72, together with the obscuration 68, absorbs any excitation light spilled from defects in the mirror coating at the right-angle reflector 58 or reflected at the interface where the excitation light 30 first enters the lens portion 24 of the sensing element 22.

The sensing element 22, discussed above in connection with FIGS. 3, 6A and 6B, can be advantageously formed as a single piece, such as by injection molding of polystyrene. As shown in FIG. 6A, the excitation light 30 entering the sensing element 22 first encounters the surface of the lens portion 124, which may be any of a number of suitable configurations such as a spherical or paraboloidal lens. The primary function of the lens portion 24 is to collimate signal recovery light 32, as shown in FIG. 6B. However, the lens portion 24 also plays a secondary role as regards the excitation light 30, essentially displacing the effective origin of the excitation light along the optical axis 45.

As described above in connection with the current state of the art, light provided by an excitation source is composed of an equilibrium distribution of ray propagation angles and tapered fiber sections are oftentimes used to match numerical apertures to a level compatible with a sensing fiber when immersed in a fluid sample. However, this approach wastes significant input energy because the angular characteristics of most of the light rays are such that they contribute only weakly to the evanescent electric field strength. Other attempts use a taper along the full length of the sensing fiber, thereby transforming low propagation angle rays at some point along the fiber to higher propagation angle rays that can contribute to the evanescent electric field. However, for these rays at lower angles to be productive, rays initially having larger propagation angles must necessarily have been lost. The continual upgrading of lower propagation angle rays by the fiber taper is obtained at the penalty of excitation light leakage along the fiber's length. This means that assay sensitivity is variable along the fiber, which can cause calibration problems. Also, light leaking from the fiber into the exterior sample could lead to fluorescence excitation of the sample itself, instead of solely from bound fluorophore molecules.

Ideally, all incoming excitation rays should be very nearly at the critical angle of a sensing fiber to maximize the evanescent electric field strength, thereby maximizing the fluorescence output by any fluorophore molecules bound to the fiber. Also, the sensing fiber should be of essentially constant diameter so that the sensitivity per unit length is constant, and with light leakage to the external environment minimized. As a practical matter, a slightly tapered sensing fiber may be required as a consequence of manufacturing processes, such as fabrication by injection molding. Typically, a taper of approximately 0.02.degrees is sufficient to assure defect-free removal of a fiber from an injection mold, and such a taper has essentially negligible optical effects. Embodiments of the present invention can provide a near-ideal situation, primarily due to characteristics of the reflector portion 26 of the sensing element 22.

Referring to FIG. 6A, the reflective surface 27 of the reflector portion 26 is constructed with an axial profile such that all rays emitted from the end of the source fiber 38 are reflected at the same angle with respect to the optical axis 45 of the sensing element 22. In other words, all rays in the sensing fiber 28 have the same propagation angle which is a highly desirable feature for an evanescent-wave-based sensor. Assuming the light source (i.e., the right-angle reflector 58 at the end of the source fiber 38) is approximately a point source, and that the angular distribution of the light emitted from that source falls within certain limits (discussed below), the shape of the requisite reflecting surface 27 can be readily mathematically derived. In practice, the point source requirement is not a difficult condition to meet, since optical fibers are available with core diameters of as small as 3.mu.m, and it is also possible to simply increase the relative size of the sensing element 22. As a practical matter, it has been found through experimentation that if the diameter of the sensing fiber 28 is about four times larger than that of the source fiber 38, then the point source condition is approximately obtained.

Figure 8:
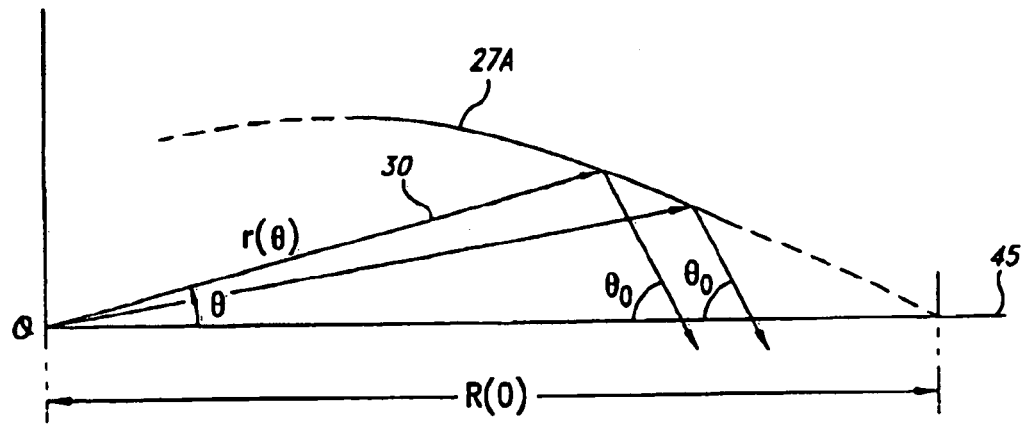
FIG. 8 depicts the geometry of a reflector portion included in the optical sensing element of FIGS. 6A and 6B.

The shape of the desired reflective surface 27 is defined by a rotation about the optical axis 45 of a curve 27A shown in FIG. 8. With a point source of light assumed at an origin O, the curve 27A can be described in accordance with the depicted polar coordinates as ##EQU1## where r(.theta.) is the distance from the origin O to the curve 27A, and .theta. is the angle between the excitation ray line 30 and the optical axis 45. The angle theta.sub.0 is the desired constant exit angle relative to the optical axis, and R(0) is the distance from the origin to the curve 27A at .theta.=0 degrees.

Figure 9:
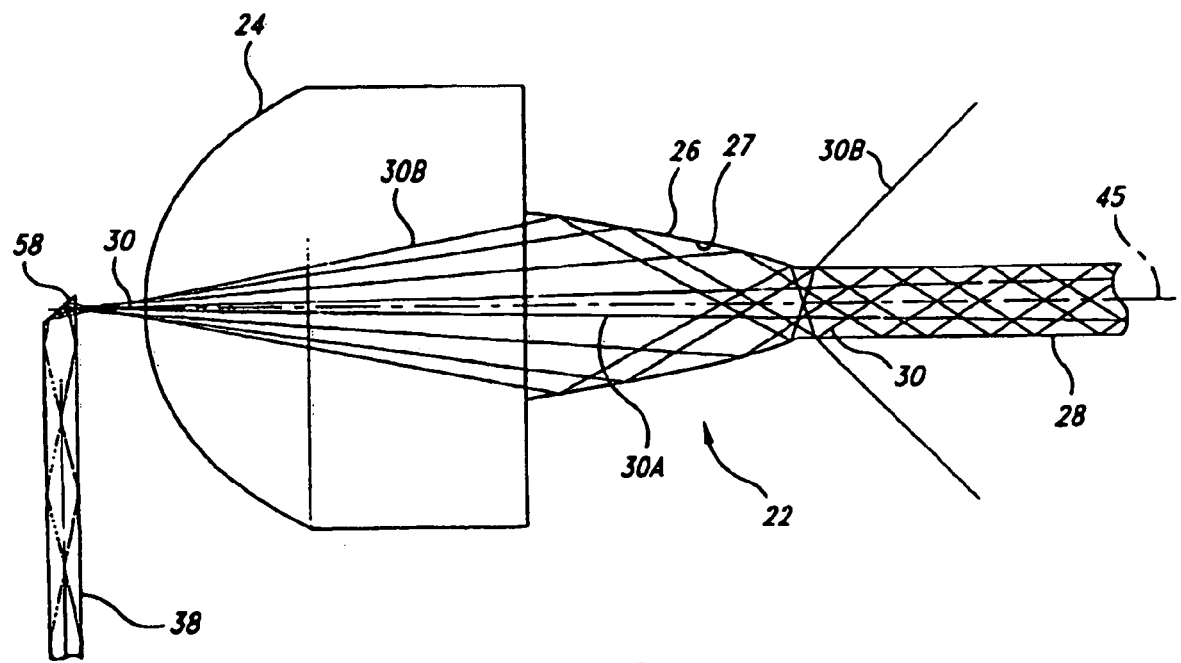
FIG. 9 is an optical ray tracing which depicts the effect of the reflector portion of FIG. 8 on excitation light rays directed at various angles.

Referring to FIG. 9, it is apparent that the reflective surface 27 performs as desired only on rays within a certain range of propagation angles. As shown, those excitation rays 30A propagating at a small angle relative to the optical axis 45 pass directly into the sensing fiber portion 28. Those rays 30B propagating at relatively large angles to the optical axis reflect off the reflective surface 27 a second time and are refracted out of the sensing element 22. However, even within these propagation angle constraints, it is not difficult to collect and direct 80-90% of the rays into the sensing fiber portion 28 at the desired angle .theta.sub.0.

The numerical aperture for a polystyrene waveguide immersed in water is about 0.856. Light rays directed at larger propagation angles will leak into the surrounding water. The greatest evanescent electric field strengths will then be produced when the excitation light propagation angle is very near the critical angle. The refractive index of polystyrene in the 600-700 nm waveband is about 1.584 leading to a critical angle of about 32.7.degrees. relative to the optical axis. As a matter of practical design, however, it may well be better to use a lower propagation angle to compensate for effects of possible misalignment associated with manufacturing tolerances, etc. A design propagation angle of approximately 2.degree. less than the critical angle is readily achieved and yields satisfactory results.

Figure 10:
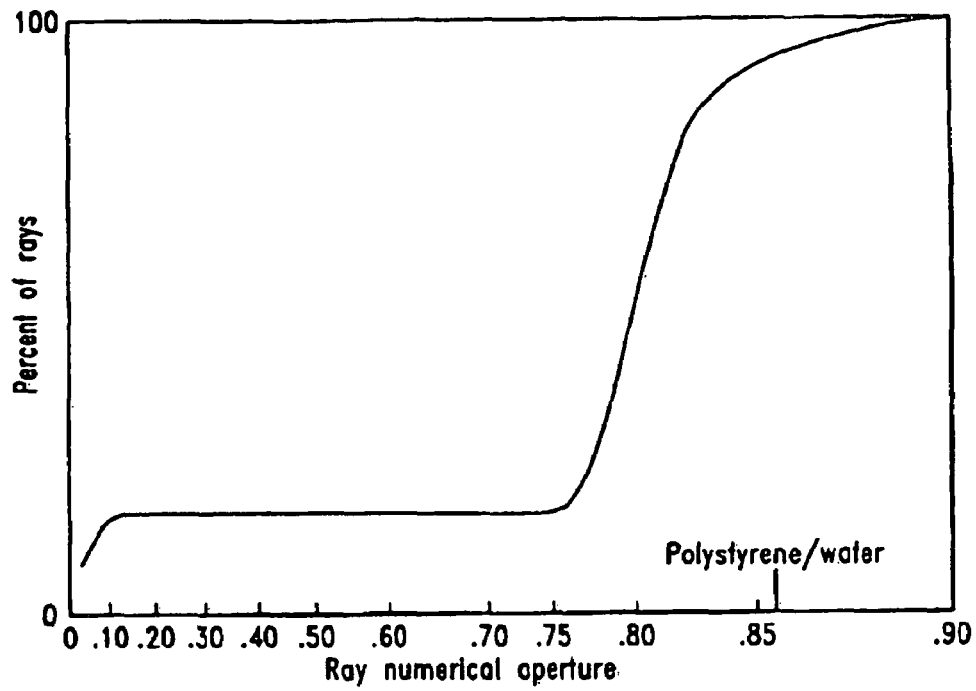
FIG. 10 is a graph that depicts the angular distribution of light rays acted on by the reflector portion of FIG. 8.

FIG. 10 depicts the cumulative angular distribution of rays entering into the sensing fiber portion 28 of the sensing element 22, as modeled with a commercial ray-tracing program, Opticad™. The particular sensing element modeled is constructed with the dimensions shown in FIG. 11, and with a 200 .mu.m diameter source fiber 38 placed 0.5 mm distant from the facing surface of the lens portion 24 of the sensing element. For purposes of modeling simplicity, it is assumed that the source fiber 38 transports rays with a uniform distribution of ray angles up to a limiting numerical aperture of 0.22.

Figure 11:
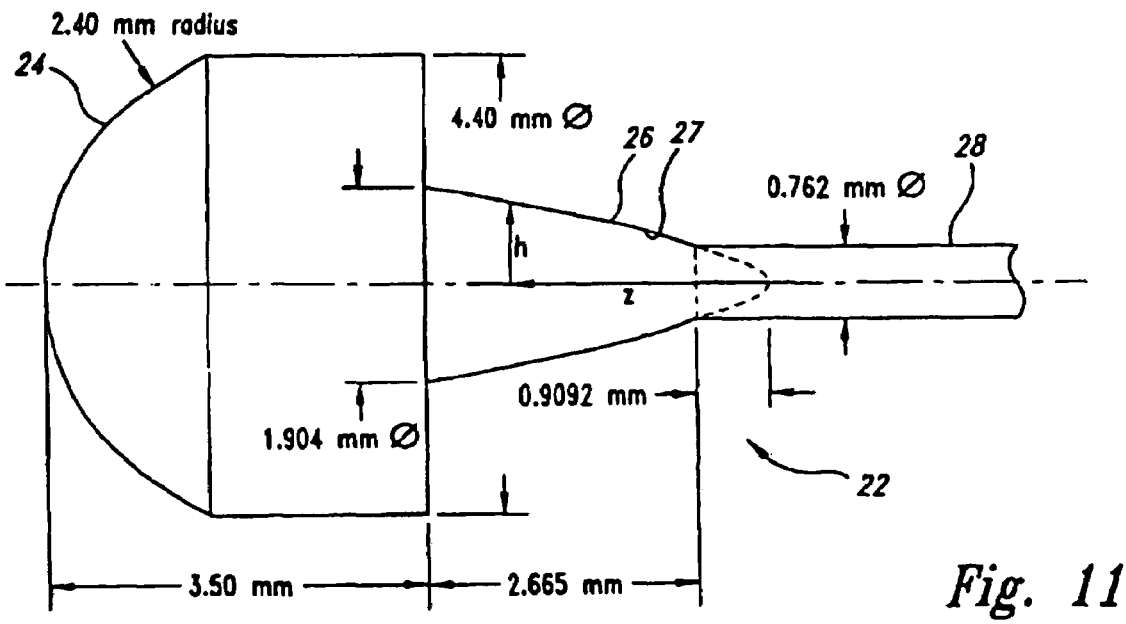
FIG. 11 identifies specific geometries of lens and reflector portions of an optical sensing element in accordance with a presently preferred embodiment of the invention.

FIG. 11 depicts the specific geometries of the integrated lens portion 24 and the reflector portion 26, which may be described with reference to a lens makers equation, $$z(\text{mm}) = 7.59178 h^2 - 1.130917 h^4 + 15.184765 h^6 - 1.276721 h^8 + 3.500005 h^{10},$$

which will be understood by those skilled in the art.

As shown in FIG. 10, the fraction of rays at small propagation angles is quite modest. Most rays are tightly clustered around the design propagation angle (expressed as a numerical aperture value of 0.81), and over 84% of the rays launched into the fiber portion 28 of the sensing element 22 have propagation angles expressed as numerical aperture values in excess of 0.75. Approximately 16% of the rays have propagation angles expressed as numerical aperture values less than 0.15, representing those rays that passed through the aspherical reflector section 26 at a low propagation angle, and hence were not acted upon by the reflector 26.

A further improvement is provided by the central obscuration 56 used in the light source module 34 shown in FIG. 4. Notably, FIG. 10 does not include the effect of this obscuration 56, which would substantially block all of the lower propagation angle rays. Because the low propagation angle light does not materially contribute to the evanescent electric field strength, it is of little value for sensing signal generation. It can, however, be a significant source of non-signal background light that must be rejected by the interrogation module 40 (see FIG. 6B). Such background flare light can come from several sources, such as fluorescence caused by a radiation of the bulk sensor material or trace impurities within it, or, alternatively, by excitation light leaking into the interrogation module 40 itself, or, alternatively, by excitation light that has been back-reflected from particles in the waveguide or from waveguide surface imperfections. Excitation rejection filters, such as the filter film 66 (see FIG. 7A), cannot be made 100% efficient. By removing low propagation angle excitation light from the system, the amount of non-signal background light in the interrogation module 40 is correspondingly reduced with little effect on the evanescent electric field excitation of surface-bound fluorophores.

Referring to FIG. 6B, it is desirable that signal recovery light 32 be collimated before it enters the interrogation module 40. The performance of the filter film 66 (see FIG. 7A) typically deteriorates if rays impinge at angles more than about plus or minus 10.degree. from the design incidence angle. Since the fluorescence process generates an isotropic distribution of ray angles from any fluorophore site, it is also desirable to collimate the wide angular distribution of rays so that they can be directed to a small, low-noise photodetector.

The fraction of signal recovery light 32 that has comparatively low propagation angles exits the sensing fiber portion 28 and passes directly through the lens 24 of the sensing element 22. The surface of the lens portion 24 and its axial placement are such that these rays emerge from the sensing fiber 28 approximately at the focal point of the lens, thereby exiting from the lens in a collimated condition. However, a second and typically larger fraction of the signal recovery light 32 exits the sensing fiber portion 28 at large propagation angles. Many of these rays then advantageously strike the reflecting surface 27 of the reflector 26, which reflects this higher propagation angle light into the lens 24, and thereafter into the optical systems included within the interrogation module 40, thereby collecting a substantial portion of recovered signal light that would have otherwise been lost. Ray modeling studies indicate that over 90% of the signal recovery light emitted from the sensing fiber 28 reaches the photodetector 64.

Any of numerous types of long-pass or band-pass filter designs may be employed for filter film 66, such as thin-film interference filters and optical crystals which can be made to transmit wavelengths above a critical wavelength and block wavelengths below that critical wavelength, or transmit within a waveband and reject over a second waveband. The simplest and most cost-effective filter film 66 may be a long-pass dichroic filter with specified filter characteristics that can be purchased from Optical Coating Laboratories of Santa Barbara, Calif. However, additional excitation blocking can be obtained in the exemplary waveband by using a spectrally-absorbing colored filter in combination with filter film 66, e.g., making plate 67 from a long-pass bulk filter material such as RG-645 or RG-665 sharp cut glass, manufactured by Schott Glass Technologies of Duryea, Pa.; or R-62, R-64, R-66, or R-68 sharp-cut filter material from Hoya Corporation; or from an organic-dyed polymer filter material exhibiting strong absorbance at the laser wavelength and low absorbance over at least a part of the fluorescence emission waveband. As previously discussed, thin-film filters as a class are not effective at attenuating rays making steep angles to the optical axis 45, whereas colored filters are, thereby providing complementary function.

With solid state laser diode excitation sources 46 commercially available in the 600 to 700 nm waveband (e.g., 638, 645, 658 nm), excitation flare may be reduced by a factor of about 1000 to 10000 times using a long-pass filter combination that exhibits 50% transmission at a wavelength about 25 nm and longer beyond the laser's emission wavelength. When excitation blocking levels of this magnitude have been reached, residual flare light levels are strongly influenced by optical defects and material inhomogeneities and may have strong fluorescence and Raman components from the laser diode and other excitation optics components subjected to high light intensities. The signal-to-noise ratio may, at this point, be most effectively influenced by placement of a laser bandpass filter in light source 34 to prevent fluorescence emission, by changing the waveguide material and its purity, by improving the optical surface quality of sensing element 22, and by moving to excitation wavelengths that do not generate strong non-signal light levels in the optical interrogation module 40. For most dielectric materials, fluorescence and internal backscattering decrease rapidly as the operating waveband is moved to longer wavelengths. To detect small fluorescence signals above these background effects, it may then be preferable to operate at the longest wavelength for which stable, high efficiency fluorophores are available.

Figure 12:
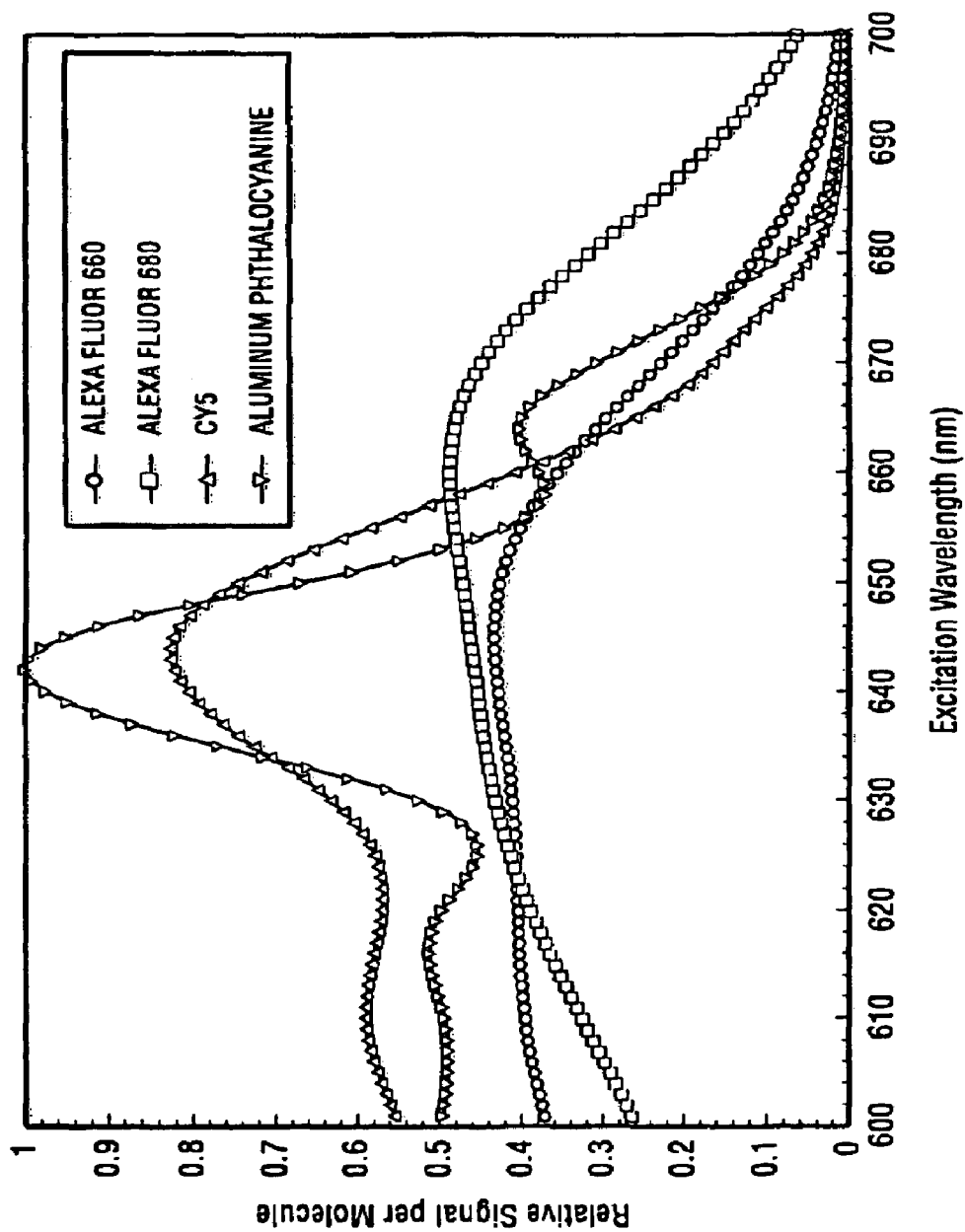
FIG. 12 is a graph that demonstrates the signal strengths associated with using different combinations of fluorophore and laser excitation wavelength.

One family of suitable molecules are the aluminum phthalocyanine compounds, disclosed in U.S. Pat. No. 5,494,793 to Schindele, et al., entitled "Monomeric Phthalocyanine Reagents". A second family of suitable molecules are the Alexa Fluor dyes available from Molecular Probes, Eugene Oreg. A third family of suitable molecules are the CyDye cyanine dyes available from Amersham Pharmacia Biotech, Inc., Piscataway, N.J. FIG. 12 shows the relative fluorescent signal strength per molecule as laser excitation wavelength is varied over the 600 nm to 700 nm waveband for four of these red fluorescent labels developed for bioassays. For this comparison, a 30 nm spectral gap between the laser and blocking filter was used. Laser diodes are commercially available at the following wavelengths from various manufacturers; 633 nm, 635 nm, 640 nm, 650 nm, 655 nm, 670 nm, 675 nm, 680 nm, 685 nm, and 690 nm. Other wavelengths may of course become available in the future and manufacturers can custom-select from production to provide wavelengths that are not at the published output wavelength. In addition, a light emitting diode excitation source may be used with suitable filtering such as a thin-film filter, to more tightly define and restrict the maximum emission wavelength.

With this understood, to obtain the best signal-to-noise ratio in a fluorescence-based evanescent-wave sensing system using inexpensive off-the-shelf excitation sources, it can be concluded from FIG. 12 that excitation wavelengths beyond 660 nm are of less interest because of their poor signal strengths and that an excitation wavelength of about 640 nm to 650 nm provides a very good match to several available fluorophores, and there are fortunately many sources available in this range.

The light that passes through the interrogation module window 60 and which has been filtered of excitation light is focused by a short focal length lens onto a suitable low-noise photodetector 64. Any lens of high light-gathering power may be used, with a particularly effective and compact design being created by a sapphire or high-index glass sphere of 1 to 10 mm diameter. Sapphire spheres of optical quality may be purchased from Edmund Scientific of Barrington, N.J. A solid-state photodiode is a suitable photodetector 64, since it is small, consumes no power, and has low noise. Light falling on the photodetector 64 is then converted to a photocurrent, which in turn is converted to a voltage using standard small-signal electronic amplification methods, such as synchronous detection. Using a 6 mm sapphire ball lens; a low-noise photodiode, type S4707-01 from Hammatsu, Inc. of Bridgewater, N.J.; and a synchronous detection amplification technique operating at an optimum chopping frequency of 135 Hz; an extremely favorable photocurrent sensitivity of 0.025 pA was realized.

Although much of the discussion above focuses on applications to evanescent-wave-based sensors, those skilled in the art will appreciate that the sensing element 22 may be suitably adapted for use in a surface plasmon resonance sensor. The ability to convert various propagation angles of light into an approximately constant propagation angle for transmission into a optical fiber is particularly advantageous for surface plasmon resonance techniques. As described above, in connection with the current state of the art, the detected resonance spectrum for currently available surface plasmon resonance sensors is the superposition of resonance spectra associated with light at various propagation angles transmitted down the sensing fiber. If, instead, light of essentially a single propagation angle is used, the resonance effect in the transmitted spectrum is much better defined, is more easily detected, and affords better quantitative analysis.

The assay system described above is readily adapted for use with surface plasmon resonance sensing operations. A light source module producing white light can be coupled to the sensing element 22 by a source fiber, an interrogation module, and an interrogation window, of substantially similar configuration to the above-described source fiber 38, interrogation module 40, and interrogation module window 60. If the surface plasmon resonance sensor fiber 114 includes a mirror 122 for returning signal light (see FIG. 1B), then an optical system much like that of the interrogation module 40 can be employed. Of course, a spectral grating and array detector (or other suitable spectrophometric devices) would be substituted for the photodetector 64 (see FIG. 6B.), and the filter 66 (see FIG. 7A) would be omitted from the design.

Removal of low propagation angle light, as in the use of the obscuration 56 of FIG. 4, provides a number of advantages to surface plasmon resonance sensing operations. Low propagation angle light does not stimulate surface plasmon waves, except in metal films too thin to readily fabricate by currently available methods. In the case of back-reflected signal light from the mirror 122 of FIG. 1B, low propagation angle light is essentially signal noise, which partly obscures the resonance effect to be measured. The reflector portion 26 of the sensing element 22 also advantageously adjusts lower propagation angle light to higher propagation angles.

Figure 2A:
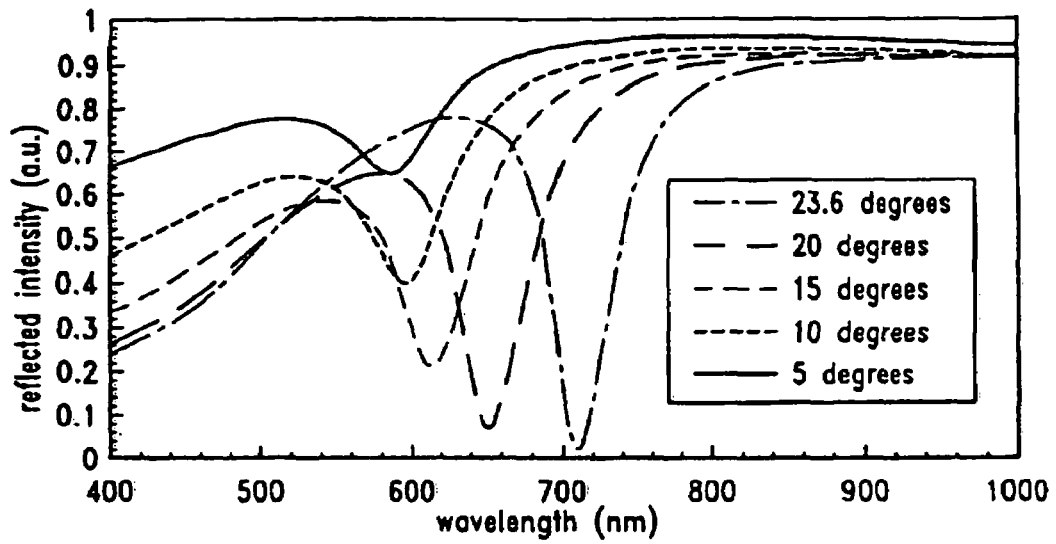
FIGS. 2A and 2B are graphs that depict theoretical resonance curves associated with use of the optical fiber of FIG. 1B in surface plasmon resonance sensing operations in accordance with the prior art.
Figure 2B:
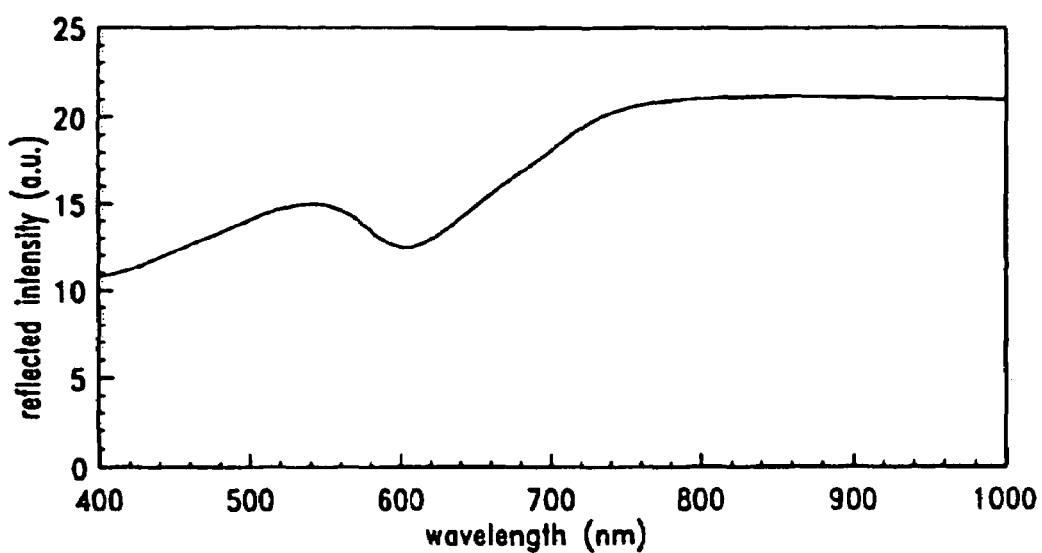
Figure 13:
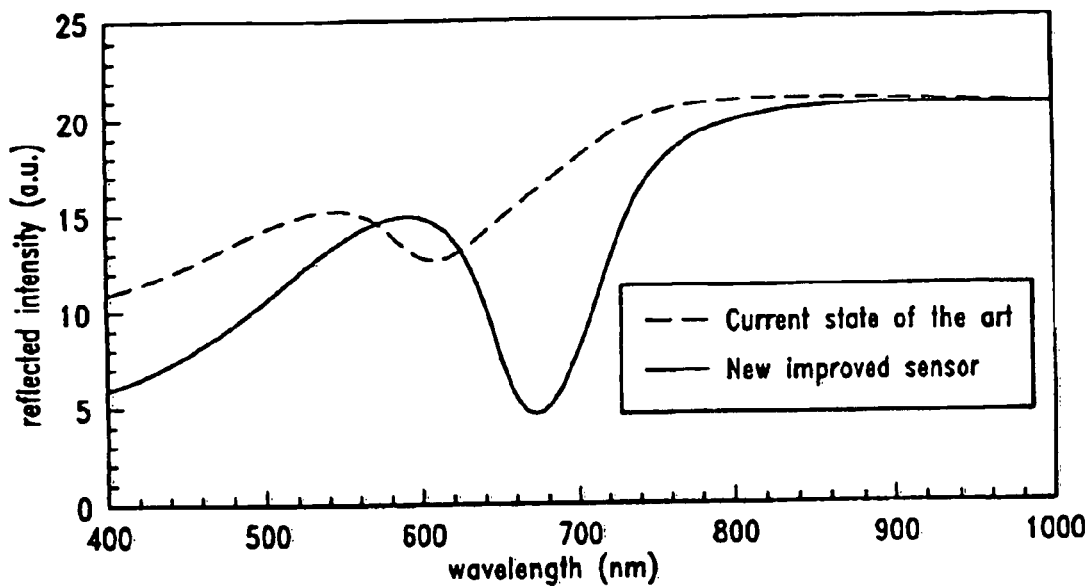
FIG. 13 is a graph that demonstrates the improved characteristics of a surface plasmon resonance sensor employing the optical sensing element of FIGS. 6A and 6B.

In accordance with ready adaptations of the embodiments described above, high numerical aperture light of approximately a constant propagation angle can be provided to a surface plasmon wave sensor. FIG. 13 shows the results of modeling a surface plasmon resonance sensor employing the optical features of the sensing element 22, as compared to the current state of the art (shown both in FIGS. 2B and 13). Assumed values include a silica optical fiber core of 400 microns having a 55 nm thick layer of gold, and a propagation angle of light of 21.60 degrees, relative to the optical axis of the fiber core, having a uniform dispersion of +−0.2 degree. The difference between the two curves illustrates the significant improvement afforded to surface plasmon resonance techniques by adaptation of the assay system described above.

Figure 14:
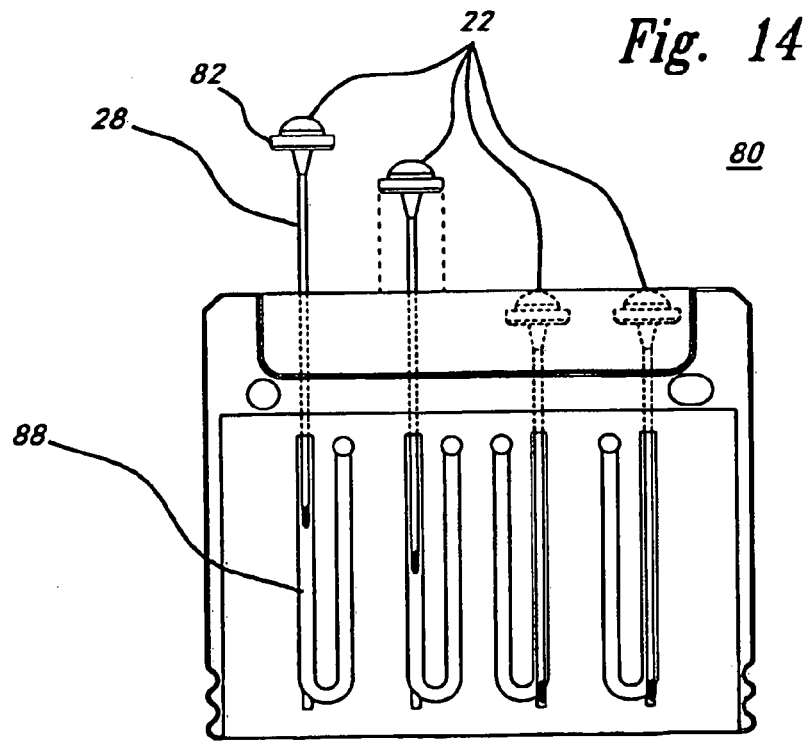
FIG. 14 depicts an assay coupon including the optical sensing element of FIGS. 6A and 6B.

FIG. 14 depicts a disposable injection molded assay card 80 which may incorporate four sensing elements 22. The four axially-interrogated sensing elements 22b may include a tab 82, which is preferably of integral, one-piece construction with the lens 24, reflector 26, and sensing fiber 28. The tab 82 assists in manipulation and placement of the sensing element 22 into a molded-in flow channel 88 in the coupon 80. In this embodiment, excitation and signal recovery are provided by four optical interrogation modules 40. The coupon 80 includes a cover 84 for sealing the molded-in flow channel 88 and a multi-needle septum 90 for introducing sample and reagent fluids into the card. The fluids may be distributed separately to each channel 88 and its axially-located sensing element 22, or the channels 88 may be joined together head-to-tail to form a single serpentine flow channel. It may be preferable to isolate the individual waveguides, at least insofar as the reagents are concerned so as to prevent cross-reactions between reagents and to allow reagent concentrations and reaction rates to be maximized. Alternatively, the card may have only one fluid chamber in which a plurality of parallel-mounted waveguides 28 are mounted.

Figure 15:
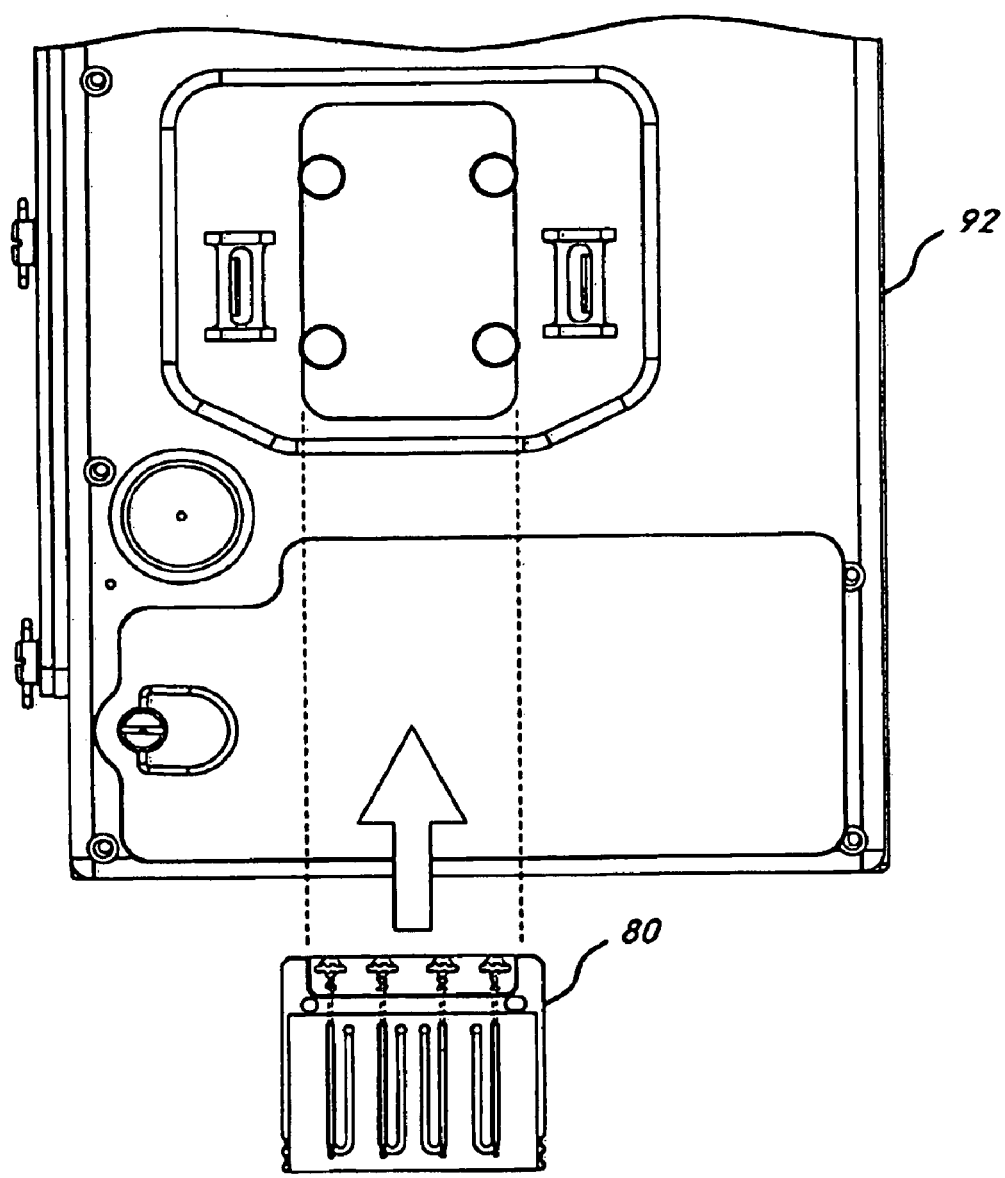
FIG. 15 depicts an assay unit in which the assay coupon of FIG. 12 may be inserted.

At the time of use, the card 80 is inserted into an assay unit (FIG. 15) in which other ancillary components of the selected assay system are included, such as multichannel peristaltic pumps for fluid control and on-board reservoirs for buffer, reagent, and waste fluids, as will be understood by those skilled in the art.

Robotic Operation

The sensing element 22 is ideally suited for use in an immersion-type assay protocol, either alone or as one element of an array of evanescent-wave probes. An immersion protocol is defined as a procedure wherein an elongate rigid sensor, such as a cylindrical waveguide, is physically immersed in one or more liquids, at least one of which contains the target substance. Optionally, the protocol may involve immersion of the waveguide in one or more additional fluids; for cleaning purposes; to create luminescence; to create or modify fluorescence in the evanescent region of the waveguide; or to modify transported optical power in the waveguide.

Many assay systems and protocols use disposable modules analogous to assay card 80 where about 1 cc or less of fluid is introduced into a fluidic structure that includes the sensing element array. An immersion protocol, however, has advantages in food safety, environmental and medical applications where the target pathogen concentration is very low or the sample is heterogenous, viscous or contains components that may foul assay apparatus. Examples of such substances include whole blood, liquefied stool samples, sewage, milk, and homogenized meat and sausage. In these cases, available sample volumes may be quite large while the acceptable pathogen level may be very low. In this situation it may be desirable to use an immersion-type assay on a large sample volume and provide means for the detector to execute a sampling pattern within the volume to improve sampling statistics. This may also better control or prevent the spread of contaminated media into complex and expensive assay fluidics that might otherwise be necessary.

Figure 1A:
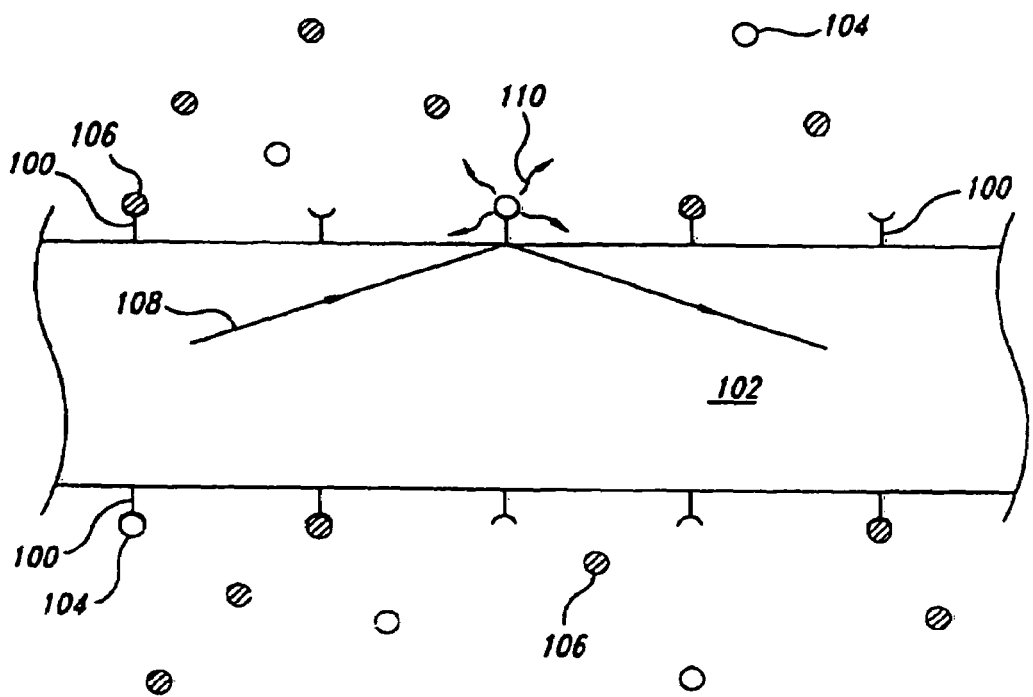
FIG. 1A depicts an optical fiber adapted for use in evanescent wave sensing operations in accordance with the prior art.
Figure 1B:
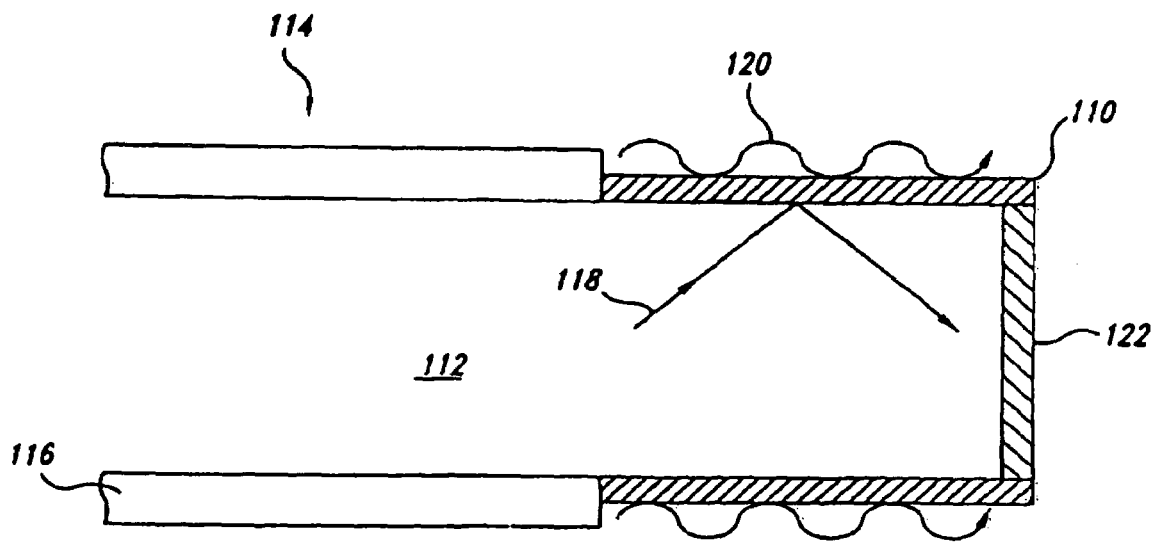
FIG. 1B depicts an optical fiber adapted for use in surface plasmon resonance sensing operations in accordance with the prior art.

Of particular interest for the detection of human pathogens in food, water and the environment is the sandwich format fluoroimmunoassay. In a typical waveguide-based sandwich immunoassay, the waveguide has a monolayer of a biological recognition element, such as capture antibody 100 immobilized on its surface as shown in FIG. 1A. The biological recognition element may be bound to the sensor 22 by a number of techniques known to those skilled in the art. In the particular case wherein sensor 22 is constructed of polystyrene and the biological recognition element is an antibody, simple physical adsorption of the antibody to the surface of the sensor provides a robust and stable means of attachment. Such monolayer-coated waveguides may maintain antibody activity for a period of months if not subjected to high temperature.

At the time of use, the waveguide is first incubated with the fluid sample that may contain the target antigen for about 1 to 5 minutes. After a wash step, the waveguide is incubated in contact with a fluorophore-labeled antibody for 1 to 5 minutes to form an antibody/antigen/labeled-antibody sandwich that will fluoresce when excitation light is passed through the waveguide.

Figure 16:
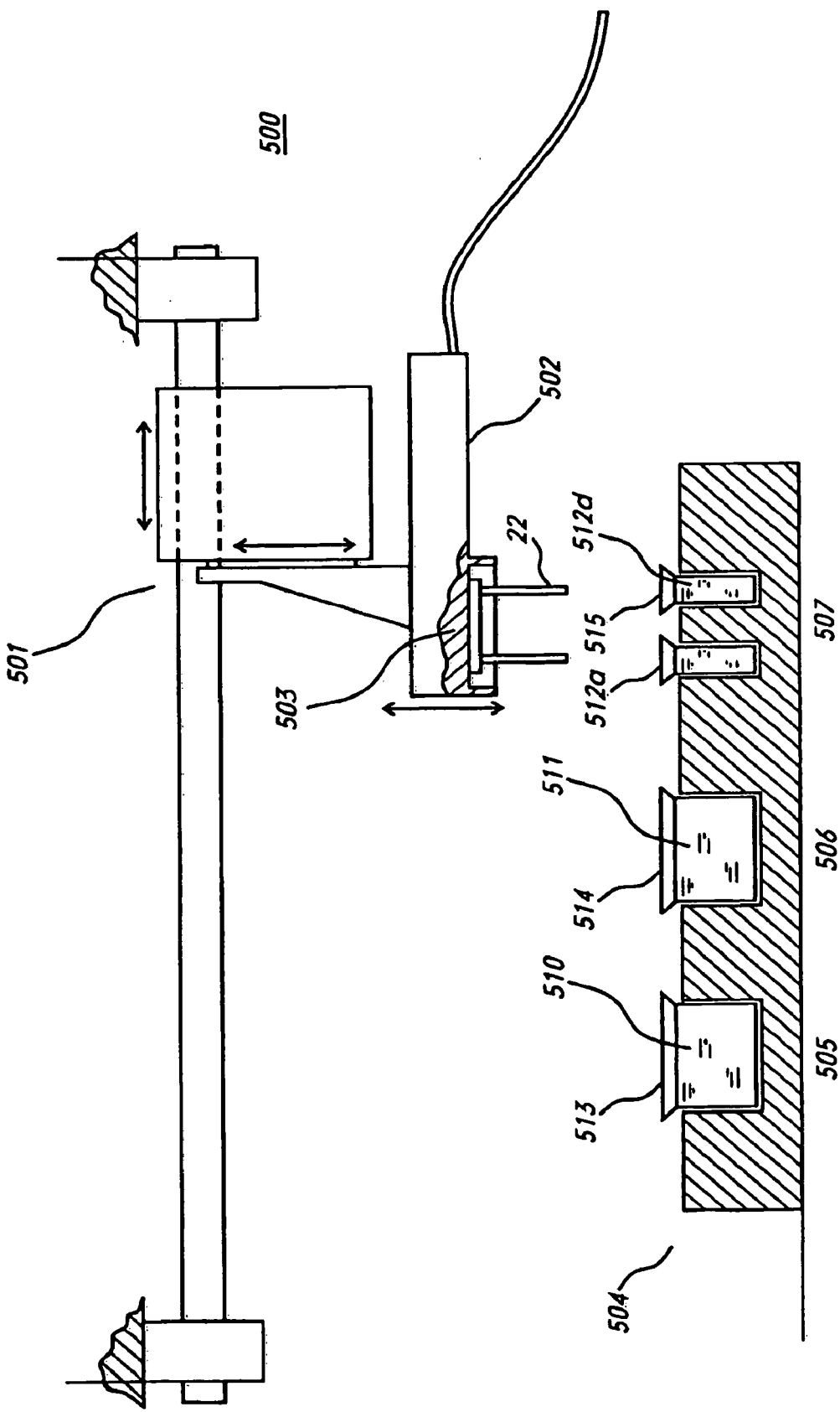
FIG. 16 depicts a robotic platform for performing immersion-type assays with cylindrical and self-collimating waveguide sensors.

One embodiment of an automated apparatus 500 for performing sandwich format immunoassays is shown in FIG. 16.

Figure 17:
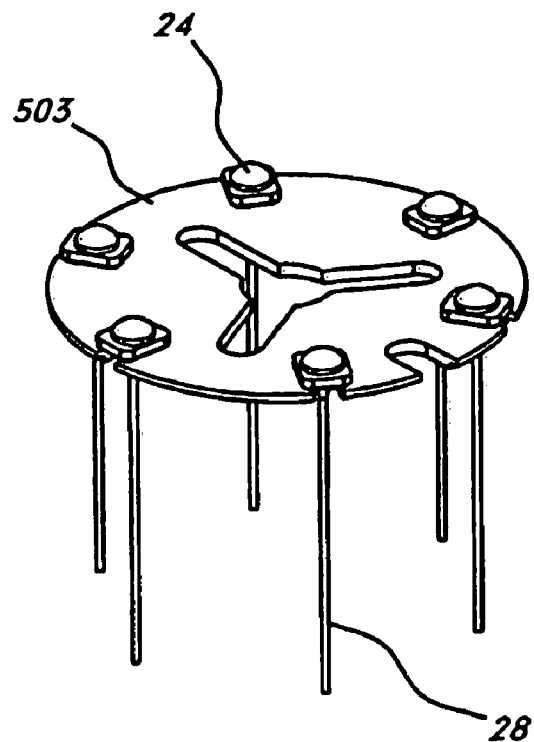
FIG. 17 depicts a carrier plate for mounting an array of six waveguides onto the robotic platform.

Apparatus 500 consists of a robotic arm 501 and an optics module 502, both under the control of embedded microcontroller 44. Robotic arm 501 provides one- or two-dimensional movement in a horizontal plane to transport a waveguide 28 array to processing stations where various liquids used in the assay are stored, and vertical motion to immerse and remove a waveguide 28 array from liquid. Optics module 502 may contain one or more sets of interrogation optics consisting of light source 34 and optical interrogation module 40. By way of nonlimiting example, there may be six separate sets of interrogation optics mounted at 60 degree intervals in a circular pattern of about 1 cm to 10 cm diameter in optics module 502. The six disposable optical sensing elements 22 in this example are shown mounted on a disposable carrier plate 503 using sonic or adhesive bonding methods in FIG. 17. The carrier plate 503 is preferably colored black and may be of a polymer material such as polystyrene, PMMA, polyvinylchloride, ABS, polycarbonate or the like, and may be from 0.5 to 2.0 mm thick and about 50 mm in diameter. Alternatively, the carrier plate 503 and sensing element 22 array may be injection molded as a one-piece transparent part. When plate 503 is mounted to the underside of optics module 502, the optical axis 45 of each optical sensing element 22 is coaxial with the corresponding optical interrogation module 40.

An assay-performing apparatus 500 for performing sandwich format fluoroimmunoassays may include an assay module 504 below the robotic arm 501 that provides three stations for performing individual assay steps; a sample station 505 for sample incubation, a washing station 506 for waveguide 28 washing, and a reagent station 507 for incubation of the waveguide 28 in a solution of fluorophore-labeled antibody reagent. To perform an assay, the robotic arm 501 first moves the waveguide 28 array to sample station 506 and immerses the array (each element of which has been coated with a capture antibody by one skilled in the art) into a disposable cup 513 of about 1 to 500 cc which has been filled with the fluid sample 510 to be examined. The array is incubated in the sample fluid 510 for a predetermined time. During this time, each waveguide 28 may be moved through a predetermined pattern by the robotic arm 501 (or by a manner to be described at a later point), so as to contact the sample volume in a statistically valid manner. Since there may be only one target material of interest, the six waveguides in this example may be coated with the same capture antibody and it is apparent that a multiwell cup holder could be provided (not shown) to increase sample throughput. Six appropriately-sized and shaped pockets would be provided in such a cup holder for six different fluid samples 510.

Referring again to FIG. 16, upon completion of this incubation step, robotic arm 501 moves the waveguide 28 array to washing station 506 and immerses the array in washing fluid 511, which may be phosphate-buffered saline with 0.1% surfactant, contained in a disposable cup 514 or in an open reservoir (not shown) that may be periodically flushed using a fluid circuit controlled by embedded microcontroller 44. Any residues of sample fluid 510 are cleaned off in this step by rapidly moving the array in a horizontal oscillatory pattern. Antigen/antibody reactions are typically sufficiently strong that this physical motion will not remove target material, but will wash off nonspecifically bound sample and reagent materials that may otherwise adversely affect assay results. At the end of this step and before removal from washing fluid 511, each waveguide 28 is interrogated with excitation light and a signal baseline is established.

Figure 18:
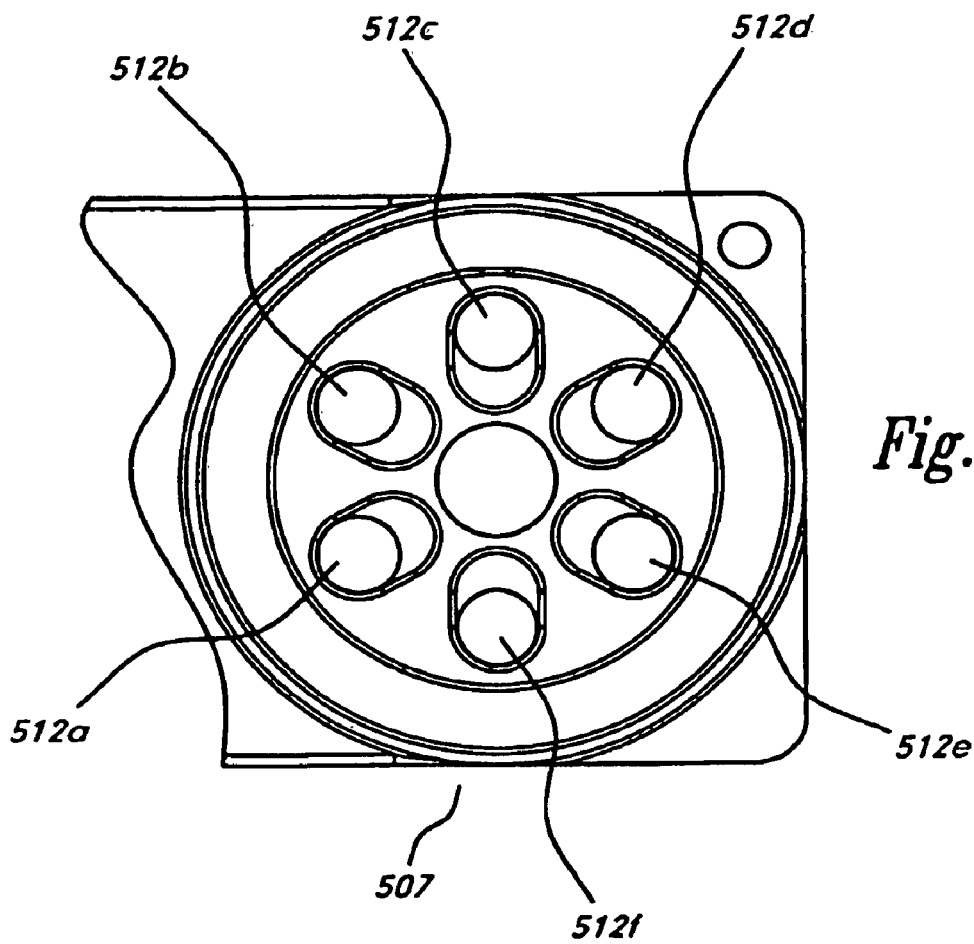
FIG. 18 depicts a 6-pocket reagent holder for performing automated waveguide assays.

Upon completion of this baseline measurement, robotic arm 501 moves the waveguide 28 array to a reagent station 507. Located at this station are a set of six nominally 0.1 to 5 cc disposable vials 515 which contain fluorophore-labeled antibody solutions 512a through 512f (FIG. 18), each vial having an axis that corresponds to a waveguide axis in the waveguide 28 array, and which may be maintained at a constant temperature through means such as a thermoelectric heating/cooling apparatus, or phase change material. Since the waveguides in waveguide 28 array may be coated with antibodies that are specific for different target materials, the vials 512a through 512f may each contain a different antibody reagent.

During a predetermined incubation period, the waveguide 28 array is periodically or continuously interrogated to monitor fluorescence signal levels. After incubation is completed, the robotic arm 501 may move the waveguide 28 array to the wash station 506, and immerse and wash the waveguides with oscillatory motion to remove any antibody reagent residues. Signal levels may be measured again at this point.

This protocol provides at least three methods for determining target material concentration. Target concentration may be monotonically related to signal rate-of-change immediately after immersion in the fluorophore-labeled reagent vials; to the change in signal level experienced during fluorophore-labeled reagent incubation; and to the change in baseline signal level as measured in the wash fluid 509, before and after fluorophore-labeled reagent incubation. The first method provides an early response, the second method may provide increased accuracy, while the third technique requires more time but allows sensitive measurements to be made even when the fluorophore-labeled reagent is strongly fluorescent.

Three-step luminescent and fluorescent assays performed on assay platform 500 are well-suited for measuring trace constituents in difficult samples such as whole blood, liquefied stool samples, sewage, milk, and homogenized meat and food products, since most contaminants are flushed off the waveguide 28 before it is immersed in the light- or fluorescence-producing reagent, allowing high sensitivity measurements to be made with minimal sample preparation. Only the distal portion of a small diameter waveguide 28 actually contacts the potentially contaminated samples, and fluids are stored in disposable cups or vials, resulting in a system that is easily maintained and used.

Figure 19:
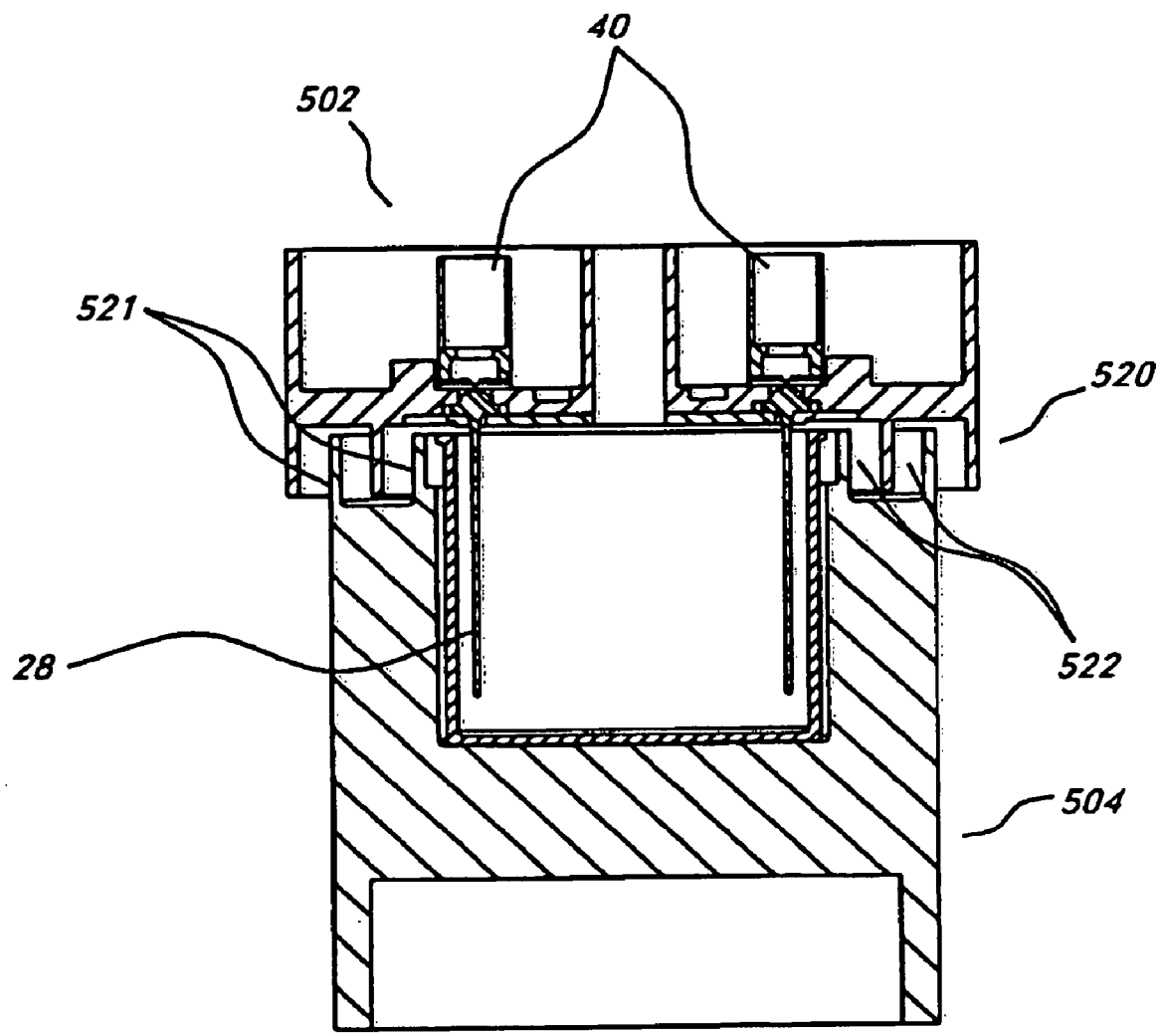
FIG. 19 depicts a contactless labyrinth seal to exclude exterior light from the waveguide array.

Extraneous room light may adversely affect low-level optical signal measurements and to prevent this from occurring, a noncontacting light-excluding labyrinth seal 520 may be used between assay module 504 and optics module 502, as shown in FIG. 19. This seal uses a series of interlaced but noncontacting annular ring walls 521 projected from both parts and separated radially by a distance at least equal to the oscillatory washing cycle length described above. External light interference is minimized when the axial separation between the interpenetrating walls is minimized, or when the annular pockets on assay module 504 are maximally deep. The latter is optically preferred but may make module 504 more difficult to clean. By way of nonlimiting example, for an array consisting of equally-spaced optical sensing elements 22 on a 4.6 cm circle, room light is excluded by labyrinth seal 520 if the annular walls 521 are 1.5 mm thick, 1 cm in axial length, and separated radially by 1 cm and axially by 1.0 mm. Other methods for minimizing external light interference while allowing lateral movement of optics module 502 relative to assay module 504 during incubation and washing include black elastomer bellows; external light shields; and synchronous signal detection. The latter electronic method can assist in nulling background light but is not preferred as a single solution at the low signal levels associated with evanescent assays.

The geometric characteristics of optical sensing element 22 are optimal for immersion assays. There is a linear relationship between signal strength and waveguide 28 immersion depth, but no corresponding relationship between signal strength and the amount of waveguide 28 protruding above the sample fluid 508 surface. This means that the interface between the optical sensing element 22 and optical interrogation module 40 can be remote from fluid contact, allowing that interface to be kept optically clean. However, an extremely long waveguide is not desirable as it may impact on mass transfer enhancement methods by making the waveguide too flexible.

A distinct advantage of the waveguide-based immersion assay method is that significant transverse fluid velocities can be generated. It is well-known to those skilled in heat and mass transfer that very high heat and mass transfer rates are possible when heat or mass is being transferred to a small-diameter cylinder or ellipse in cross-flow. This is attributable to a greatly reduced mass transfer boundary layer thickness in cross-flow due to short fluid element residence times. This means the target species can penetrate closer to the object's surface and, when applied to a bioassay, will have a higher probability of reacting with constituents such as capture antibodies in the evanescent layer. By contrast, it is very difficult to enhance mass transfer in a coaxial flow geometry such as in assay card 80 because flow is typically laminar and a thick mass transfer boundary layer builds up at the waveguide 28 surface because of the parallel flow geometry and long fluid contact time.

Figure 20:
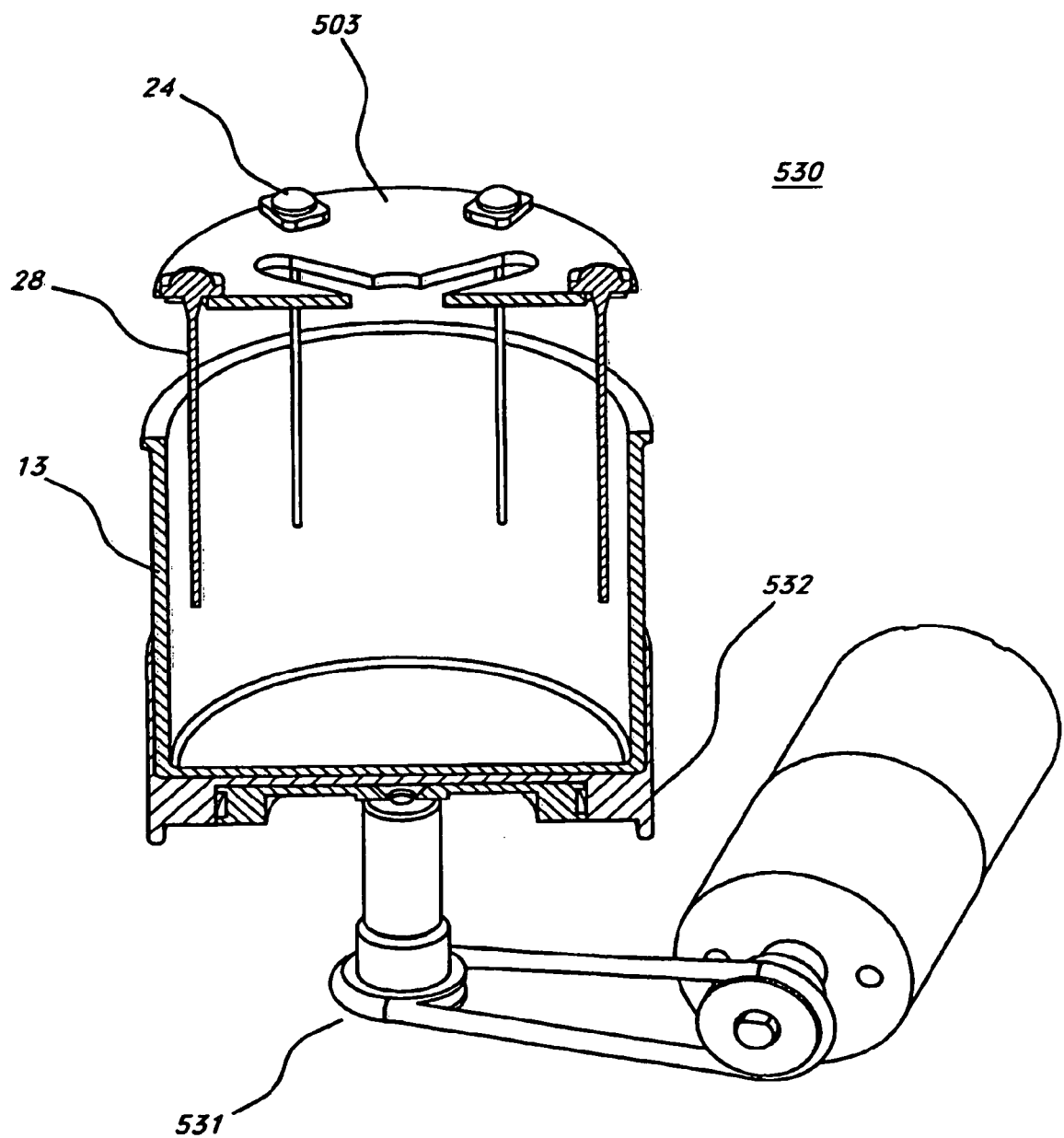
FIG. 20 depicts a rotary sample stage for maximizing sample contact with the waveguides and enhancing mass transfer to the waveguide surfaces.

One method for mass transfer enhancement with assay-performing apparatus 500 has been previously described, namely oscillatory lateral movement of waveguide 28. A second method particularly suited to large homogenized food samples is to modify sample station 505 to provide rotary motion of sample cup 513. FIG. 20 shows in sectional view a sample cup 513 on such a motorized stage 530. The station includes a motorized drive 531, under control of embedded microcontroller 44, and turntable 532 upon which sample cup 513 is placed. The waveguide 28 array is positioned coaxial to sample cup 513, with individual elements adjacent to and equally spaced from the cup perimeter, where fluid velocities are a maximum. Since the waveguide 28 array is disposed in a symmetric circular pattern, each array element experiences the same fluid movement and by rotating the cup clockwise and counterclockwise for equal time periods, each side of waveguide 28 is uniformly subjected to the effects of flow. At very low velocities, flow enhancement may come primarily from bulk fluid movement. At higher velocities the array elements will begin to shed vortices which augment sample mixing. The sample cup 513 may also be molded with built-in vanes and features that serve to circulate and mix sample throughout the volume, or a mechanical stirring means, such as magnetic stir bar, may be added to facilitate sample circulation.

Figure 21:
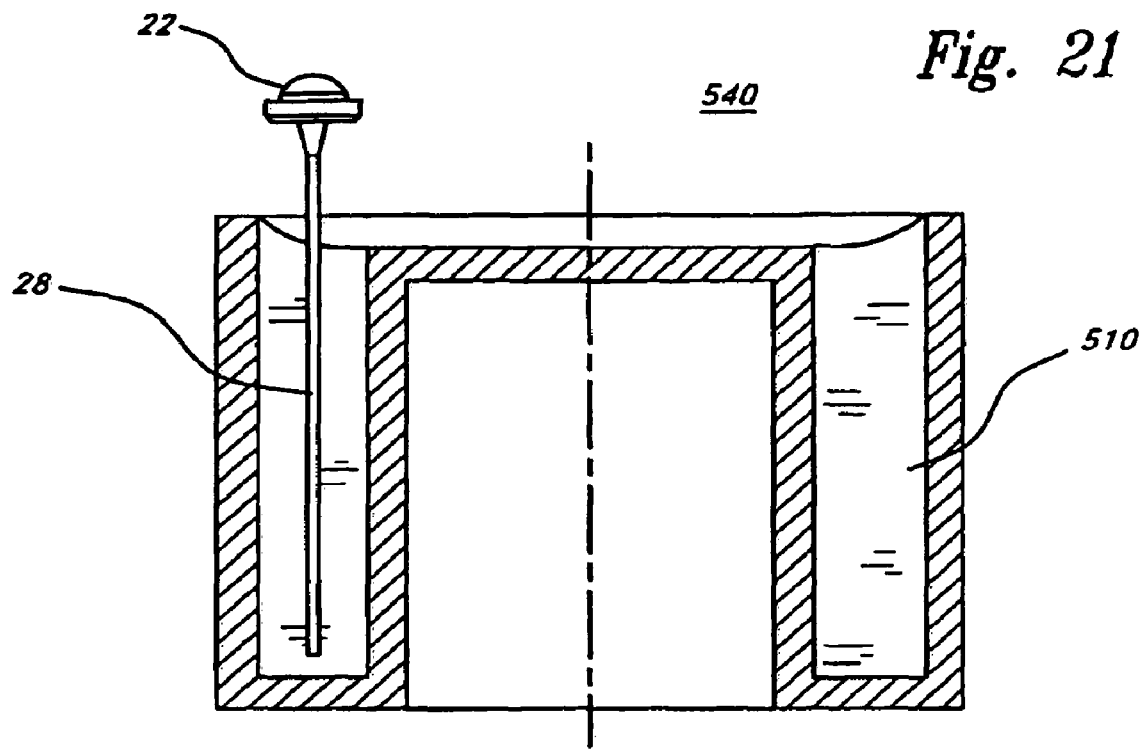
FIG. 21 depicts an annular sample cup that allows higher rotational speeds and greater mass transfer enhancements by reducing fluid climb on the outermost cup wall.

Rotational rates and mass transfer enhancement may be limited to a perimeter velocity of about 25 cm/sec for simple cups. At that perimeter velocity a water-based sample fluid 510 will climb up the cup wall about 0.25 cm, and may spill over the cup's edge. Considerably higher perimeter velocities can be reached with the annular cup 540 shown in FIG. 21 without danger of spilling. In the absence of surface tension effects, the climb height h is given by $$h = (2\pi^2 F^2)(R_1^2 - R_0^2)/g$$

Where f is the rotational rate and $R_0$ and $R_1$ are the inner and outer radii of the annular space, respectively. As a non-limiting example, if the outer radius is 2.35 cm and the inner radius is 1.85 cm, then for a maximum tolerable climb height of 2.5 mm, the calculated maximum permissible velocity increases by a factor of 1.7 times. An experimental test under these conditions yielded a higher velocity enhancement, of 2.0 times. This was due in part to a surface tension-related leveling that occurs with small gaps, a beneficial effect which is not included in the previous equation.

Figure 22:
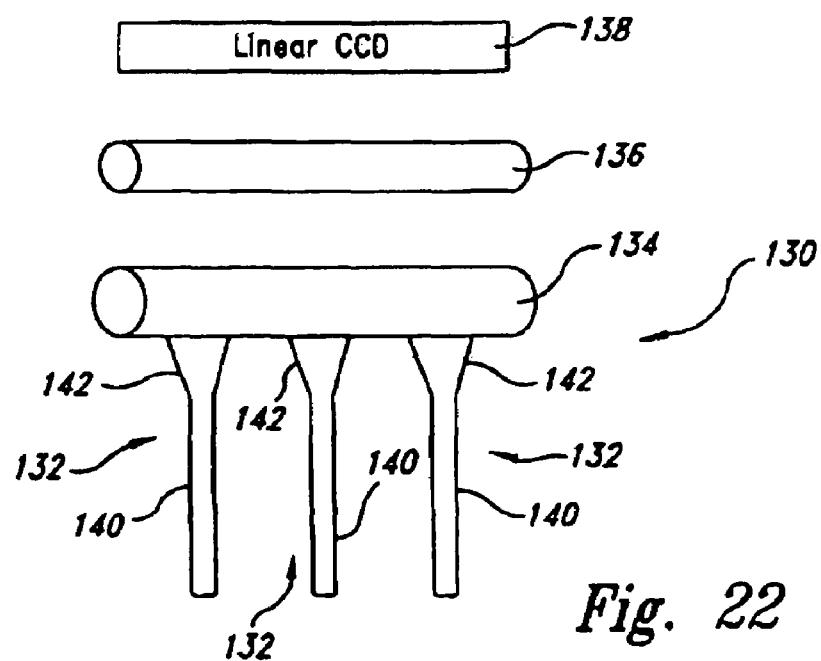
FIG. 22 depicts a multi-element sensor in accordance with an embodiment of the present invention.

It will be appreciated that, although embodiments of the invention have been described for purposes of illustration, various modifications may be made without deviating from the spirit and scope of the invention. For example, FIG. 22 depicts a multi-element sensor 130 having a plurality of approximately parallel sensing elements 132 formed as a single unit in combination with a single cylindrical lens portion 134. The cylindrical lens portion 134 is functionally substituted for the lens portion 24 described above; a cylindrical lens 136 is functionally substituted for the sapphire ball lens 62; and, an array of photodiodes or a linear charge-coupled device 138 is functionally substituted for the photodetector 64. The sensing elements 132 each include a slab waveguide portion 140 and two-dimensional reflector portion 142, with reflecting side surfaces defined mathematically like the reflective surface 27 described above. Advantages of the multi-element sensor 130 may include improved manufacturability, more flexible design parameters, improved waveguide power densities, and greater sensing surface area to test sample volume, thereby improving signal to noise characteristics.

As another example, any of a variety of lens configurations can be functionally substituted for the GRIN lens 52 described in connection with FIG. 4. Blocking low propagation angle light can be readily accomplished by a compound lens configuration, including paired planoconcave lenses forming highly collimated light, in which an obscuration is selectively positioned.

Particular optical structures, such as optical fibers, refractive surfaces and reflective surfaces have been described in connection with certain embodiments of the present invention. However, those skilled in the art will appreciate any number of light-directing media and devices that can be suitably adapted and combined to achieve the above-described effects and functions. For example, any of a wide variety of waveguides may be adapted for use as sensing elements. Also, metalized mirror reflecting surfaces may be substituted for the described dielectric surfaces. Reflective surfaces may be substituted for refractive surfaces, and vice versa.

The above-described embodiment of the reflector 26, whether alone or in combination with the lens 24, functions essentially as a light ray redirection device, which adjusts or otherwise modifies the propagation angle of light. The above-described embodiment of the light source module 34 includes, by virtue of features associated with the described lens 52 and obscuration 56, a light selection functionality in which certain ranges of light propagation angles may be blocked, passed, or otherwise selected for provision to subsequent light processing components. The above-described embodiments of the source fiber 38 and, in part, the sensing fiber 28 function as light transfer devices. Those skilled in the art will appreciate that a wide variety of alternative media, elements, and devices can be functionally substituted for these particular described embodiments.

Those skilled in the art will appreciate that various embodiments of the invention may be applied in fields other than assay methods and apparatus. Additionally, distinguishing between components such as a light source module and sensing element is somewhat arbitrary, since certain of the features described in connection with the sensing element could be suitably adapted to form a part of a light source module. Further, although the description above identifies "optical" features and effects, the invention encompasses any of a wide variety of equivalent features and effects associated with other parts of the electromagnetic spectrum, including light other than visible light.

These and other variations can be made to the invention in light of the detailed description above. In general, in the following claims, the terms used should not be construed to limit the invention to the specific embodiments disclosed in the specification, but should be construed to include all energy-directing media and devices that operate under the claims to provide associated signal transfer, retention, and detection characteristics. Accordingly, the invention is not limited by the disclosure, but instead its scope is to be determined entirely by the following claims.

While the preferred embodiment of the invention has been illustrated and described, it will be appreciated that various changes can be made therein without departing from the spirit and scope of the invention.

When the phrase "at least one [specified element] that is selected from the group consisting of" is used in any of the claims, that phrase is defined to mean that any one, any more than one, or all, of the listed things or steps following that phrase is, or are, part of the claimed invention. For example, if a hypothetical claim recited "at least one [specified element] that is selected from the group consisting of A, B, and C", then the claim is to be interpreted so that the [specified element] may comprise an A alone, a B alone, a C alone, both A and B, both A and C, both B and C, or all of A, B and C.

The words "means for" must appear in a claim before that claim is construed as claiming a means for performing a specified function under 35 USC section 112, sixth paragraph.

It is understood that the foregoing forms of the invention were described and illustrated strictly by way of non-limiting example. As used herein, except in the claims, the words "and" and "or" are each defined to also carry the meaning of "and/or".

The embodiments of the invention in which an exclusive property or privilege is claimed are defined as follows:

1. An optical assay apparatus for detecting an analyte in a sample, said optical assay apparatus comprising:
   (a) a light source module operable to produce an output of excitation light rays having respective wavelengths that fall in a range from about 600 nm to about 700 nm;
   (b) an optical sensor optically coupled with said light source module, wherein said optical sensor comprises a light ray redirection portion and an assay sensing portion; wherein said assay sensing portion comprises a sensing waveguide and a sensor chemistry coating on said sensing waveguide; wherein said sensing waveguide comprises an input end and an optical axis at said input end; wherein said light ray redirection portion is operable to receive at least some of said excitation light rays produced by said light source module and to correspondingly provide to said sensing waveguide an output of reflected excitation light rays directed at an approximately constant angle with respect to said optical axis at said input end of said sensing waveguide; wherein, during use of said optical assay apparatus, said sensor chemistry coating comprises a fluorophore, at least some of said output of reflected excitation light rays passes through said sensing waveguide and creates an evanescent electric field in said sensor chemistry coating, said fluorophore emits an output of signal recovery light rays in response to said evanescent electric field as a function of a presence of said analyte in said sample, and said sensing waveguide transports a collected portion of said signal recovery light rays; and
   (c) an interrogation module optically coupled with said optical sensor and operable to receive from said sensing waveguide at least some of said collected portion of said signal recovery light rays; wherein said interrogation module comprises:
      (i) a photodetector; and
      (ii) a filter; wherein said filter is located between said photodetector and said optical sensor, and is selected to block greater than about 99.9 percent of said respective wavelengths of said excitation light rays produced by said light source module and to have a transmission of greater than about 50 percent at wavelengths longer than a wavelength that is at least about 25 nm longer than a longest one of said respective wavelengths of said excitation light rays produced by said light source module, to enable said filter to minimize how many of said excitation light rays produced by said light source module reach said photodetector from said filter, while maximizing how many of said signal recovery light rays in said collected portion of said signal recovery light rays reach said photodetector from said filter; and wherein said photodetector is operable to generate a corresponding output signal from said signal recovery light rays that reach said photodetector from said filter.

2. The apparatus of claim 1, wherein said respective wavelengths of said excitation light rays produced by said light source module fall in a range from about 638 nm to about 650 nm.

3. The apparatus of claim 1, wherein said fluorophore has an absorbance that falls in a wavelength range from about 635 nm to about 700 mm.

4. The apparatus of claim 3, wherein said fluorophore comprises at least one fluorophore component that is selected from the group consisting of a synthetic dye of a cyanine type that has maximum excitation effectiveness at 649 nm and emits fluorescent light maximally at 670 nm, a fluorescent dye that has maximal absorption at 663 nm and maximal fluorescent emission at 690 nm, a fluorescent dye that has maximal absorption at 679 nm and maximal fluorescent emission at 702 nm, and an aluminum phthalocyanine compound.

5. The apparatus of claim 1, wherein said signal recovery light rays emitted by said fluorophore have respective wavelengths that fall in a range from about 635 nm to about 800 nm.

6. The apparatus of claim 1, wherein said respective wavelengths of said excitation light rays produced by said light source module are selected to maximize a signal strength of said signal recovery light rays emitted by said fluorophore.

7. The apparatus of claim 1, wherein said filter comprises at least one filter component that is selected from the group consisting of a laser line-rejection filter film, a long pass dichroic filter film, a spectrally-absorbing bulk filter, a colored glass bulk filter, a colored polymer bulk filter, and a long pass filter comprising a filter film and a bulk filter.

8. A method for moving an optical sensor with respect to at least one assay station; wherein said method comprises the steps of:
   (a) providing an optical assay apparatus comprising:
      (i) a light source module operable to produce an output of excitation light rays;
      (ii) an optical sensor optically coupled with said light source module and operable to receive at least some of said excitation light rays produced by said light source module; wherein said optical sensor comprises a sensing waveguide and a sensor chemistry coating on said sensing waveguide; wherein, during said assay, said sensor chemistry coating comprises a fluorophore, at least some of said excitation light rays from said light source module pass through said sensing waveguide and create an evanescent electric field in said sensor chemistry coating, said fluorophore emits an output of signal recovery light rays in response to said evanescent electric field as a function of a presence of said analyte in said sample fluid, and said sensing waveguide transports a collected portion of said signal recovery light rays; and (iii) an interrogation module optically coupled with said optical sensor and operable to receive from said sensing waveguide at least some of said collected portion of said signal recovery light rays; wherein said interrogation module generates a corresponding output signal from said signal recovery light rays received by said interrogation module from said sensing waveguide;

(b) providing at least one assay station that is selected from the group consisting of a sample station, a washing station and a reagent station; wherein, during said assay, said sample station, said washing station and said reagent station are operable to contain a respective fluid, namely, said sample fluid, a washing fluid, and a reagent fluid comprising a fluorophore-labeled reagent that is labeled with said fluorophore;

(c) moving said optical sensor into a position over said respective fluid in said at least one assay station;

(d) moving said optical sensor towards said respective fluid in said at least one assay station until at least part of said sensor chemistry coating on said sensing waveguide is immersed in said respective fluid in said at least one assay station; and (e) removing said optical sensor from said respective fluid in said at least one assay station, to eliminate a need to transfer said respective fluid into or out of said at least one assay station while said assay is being performed.

9. The method of claim 8, wherein said method further comprises the steps of first performing steps (c), (d) and (e), wherein said respective fluid is selected from the group consisting of said sample fluid and said reagent fluid; and then performing steps (c), (d) and (e) wherein said respective fluid is said washing fluid.

10. The method of claim 8, wherein said method further comprises the steps of first performing steps (c), (d) and (e), wherein said respective fluid is selected from the group consisting of said sample fluid and said washing fluid; and then performing steps (c), (d) and (e) wherein said respective fluid is said reagent fluid.

11. The method of claim 8, wherein said method further comprises the steps of first performing steps (c), (d) and (e), wherein said respective fluid is said sample fluid; then performing steps (c), (d) and (e), wherein said respective fluid is said washing fluid; and then performing steps (c), (d) and (e), wherein said respective fluid is said reagent fluid.

12. The method of claim 8, wherein said method further comprises the step of performing steps (c), (d) and (e) automatically by using a robotic transporter for moving and removing said optical sensor.

13. The method of claim 8, wherein in step (d) said respective fluid is selected from the group consisting of said sample fluid and said reagent fluid; and wherein, while said sensor chemistry coating on said sensing waveguide is immersed in said respective fluid in step (d), said method further comprises the step of exposing said sensor chemistry coating on said sensing waveguide to at least substantially all of said sample fluid in said sample station or said reagent fluid in said reagent station, to increase a probability of an interaction between said sensor chemistry coating and said analyte in said sample fluid or said fluorophore-labeled reagent in said reagent fluid to, in turn, increase an assay sensitivity of said method.

14. The method of claim 8, wherein said method further comprises the step of providing for said at least one assay station a respective at least generally annular container having an at least generally annular volume for said respective fluid contained by said at least one assay station.

15. The method of claim 8, wherein in step (d) said respective fluid is selected from the group consisting of said sample fluid and said reagent fluid, and while said sensor chemistry coating on said sensing waveguide is immersed in said respective fluid in step (d), said method further comprises the step of increasing a reaction rate between said sensor chemistry coating on said sensing waveguide and said analyte in said sample fluid or said fluorophore-labeled reagent in said reagent fluid by providing a relative motion between said sensor chemistry coating and said sample fluid or said reagent fluid, wherein said relative motion increases a mass transfer to said sensor chemistry coating of said analyte in said sample fluid or said fluorophore-labeled reagent in said reagent fluid, by decreasing a mass transfer boundary layer thickness between said sensor chemistry coating and said sample fluid or said reagent fluid.

16. The method of claim 15, wherein said sensing waveguide has a long axis; and wherein said method further comprises the step of oscillating said optical sensor in a direction that is at least generally perpendicular to said long axis of said sensing waveguide, to provide said relative motion between said sensor chemistry coating on said sensing waveguide and said sample fluid or said reagent fluid.

17. The method of claim 15, wherein said sensing waveguide has a long axis; and wherein said method further comprises the step of providing a flow of said sample fluid or said reagent fluid; wherein said flow is in a direction which is at least generally perpendicular to said long axis of said sensing waveguide, to provide said relative motion between said sensor chemistry coating on said sensing waveguide and said sample fluid or said reagent fluid.

18. The method of claim 15, wherein said at least one assay station is selected from the group consisting of said sample station and said reagent station; and wherein said method further comprises the steps of providing said sample station with a sample container for said sample fluid or providing said reagent station with a reagent container for said reagent fluid; and then rotating said sample container or said reagent container to, in turn, rotate said sample fluid in said sample container or said reagent fluid in said reagent container, to provide said relative motion between said sensor chemistry coating on said sensing waveguide and said sample fluid or said reagent fluid.

19. The method of claim 15, wherein said at least one assay station is selected from the group consisting of said sample station and said reagent station; and wherein said method further comprises the steps of providing said sample station or said reagent station with a mechanical stirrer; and then using said mechanical stirrer for circulating said sample fluid in said sample station or said reagent fluid in said reagent station, to provide said relative motion between said sensor chemistry coating on said sensing waveguide and said sample fluid or said reagent fluid.

20. The method of claim 15, wherein said method further comprises the steps of providing a flow of said sample fluid or said reagent fluid, wherein said flow has a direction; and then periodically reversing said direction of said flow, to provide said relative motion between said sensor chemistry coating on said sensing waveguide and said sample fluid or said reagent fluid.

* * * * *